United States Patent
Abbott et al.

(10) Patent No.: US 8,895,570 B2
(45) Date of Patent: Nov. 25, 2014

(54) PURINE DERIVATIVES

(75) Inventors: Phillip Abbott, Cheshire (GB); Roger Victor Bonnert, Cheshire (GB); Thomas McInally, Cheshire (GB); Stephen Thom, Cheshire (GB); Hiroki Wada, West Bridgeford (GB); Satoshi Onuma, Osaka (JP)

(73) Assignee: AstraZeneca AB, Soderitalje (SE)

( * ) Notice: Subject to any disclaimer, the term of this patent is extended or adjusted under 35 U.S.C. 154(b) by 34 days.

(21) Appl. No.: 13/994,321

(22) PCT Filed: Dec. 14, 2011

(86) PCT No.: PCT/GB2011/052476
§ 371 (c)(1),
(2), (4) Date: Aug. 30, 2013

(87) PCT Pub. No.: WO2012/080730
PCT Pub. Date: Jun. 21, 2012

(65) Prior Publication Data
US 2013/0338174 A1    Dec. 19, 2013

Related U.S. Application Data

(60) Provisional application No. 61/424,171, filed on Dec. 17, 2010.

(51) Int. Cl.
*A61K 31/52* (2006.01)
*C07D 473/18* (2006.01)

(52) U.S. Cl.
CPC ............................ *C07D 473/18* (2013.01)
USPC .......................... 514/263.22; 544/276

(58) Field of Classification Search
CPC .................................................. C07D 473/18
See application file for complete search history.

(56) References Cited

U.S. PATENT DOCUMENTS

| | | | |
|---|---|---|---|
| 4,179,562 A | 12/1979 | Ponsford | |
| 4,689,338 A | 8/1987 | Gerster | |
| 4,698,348 A | 10/1987 | Gerster | |
| 4,714,701 A | 12/1987 | Beauchamp | |
| 4,912,112 A | 3/1990 | Seydel et al. | |
| 5,736,549 A | 4/1998 | Beasley et al. | |
| 5,994,361 A | 11/1999 | Penney et al. | |
| 6,028,076 A | 2/2000 | Hirota et al. | |
| 6,110,923 A | 8/2000 | Ely | |
| 6,329,381 B1 | 12/2001 | Kurimoto et al. | |
| 6,376,501 B1 | 4/2002 | Isobe et al. | |
| 6,448,236 B1 | 9/2002 | Monaghan | |
| 6,458,798 B1 | 10/2002 | Fujita et al. | |
| 6,630,478 B2 | 10/2003 | Diamond et al. | |
| 6,887,880 B2 | 5/2005 | Levy et al. | |
| 6,951,866 B2 | 10/2005 | Fujita et al. | |
| 7,157,465 B2 | 1/2007 | Isobe et al. | |
| 7,521,454 B2 | 4/2009 | Isobe et al. | |
| 7,642,350 B2 | 1/2010 | Pryde | |
| 7,691,877 B2 | 4/2010 | Jones et al. | |
| 7,754,728 B2 | 7/2010 | Isobe et al. | |
| 8,012,964 B2 | 9/2011 | Kurimoto et al. | |
| 8,138,172 B2 | 3/2012 | Cook et al. | |
| 2002/0040032 A1 | 4/2002 | Glasky et al. | |
| 2002/0061899 A1 | 5/2002 | Diamond et al. | |
| 2002/0068745 A1 | 6/2002 | Levy et al. | |
| 2002/0128264 A1 | 9/2002 | Taylor | |
| 2003/0018261 A1 | 1/2003 | Bae | |
| 2003/0105323 A1 | 6/2003 | Fujita et al. | |
| 2003/0144283 A1 | 7/2003 | Coleman et al. | |
| 2003/0191086 A1 | 10/2003 | Hanus et al. | |
| 2003/0212092 A1 | 11/2003 | Heppner et al. | |
| 2004/0019048 A1 | 1/2004 | Crooks et al. | |

(Continued)

FOREIGN PATENT DOCUMENTS

| | | |
|---|---|---|
| CA | 1220148 A1 | 4/1987 |
| CN | 101239980 A | 8/2008 |

(Continued)

OTHER PUBLICATIONS

American Cancer Society. "Cancer Types." © 2013. Available from: < http://www.cancer.org/cancer/showallcancertypes/index >.*
Baade, P., et al. "One in four cancers preventable—but first we need the willpower." © Mar. 19, 2012. Available from: < http://theconversation.com/one-in-four-cancers-preventable-but-first-we-need-the-willpower-5850 >.*
Mayo Clinic. "Prostate cancer prevention: What you can do." © Dec. 6, 2008. Available from: < http://web.archive.org/web/20081206101911/http://www.mayoclinic.com/health/prostate-cancer-prevention/MC00027 >.*

(Continued)

*Primary Examiner* — Noble Jarrell
*Assistant Examiner* — John S Kenyon
(74) *Attorney, Agent, or Firm* — Finnegan, Henderson, Farabow, Garrett & Dunner LLP

(57) ABSTRACT

The invention provides the compound of formula (I) and pharmaceutically acceptable salt thereof, pharmaceutical compositions containing the compound and the use of the compound in therapy.

(I)

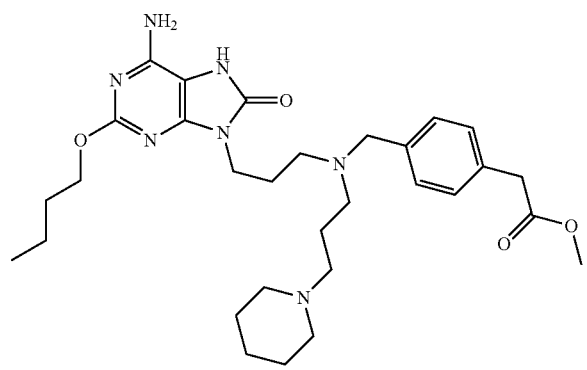

9 Claims, 6 Drawing Sheets

(56) References Cited

U.S. PATENT DOCUMENTS

| | | |
|---|---|---|
| 2004/0132748 A1 | 7/2004 | Isobe et al. |
| 2004/0204438 A1 | 10/2004 | Crooks et al. |
| 2004/0214192 A1 | 10/2004 | Hashida et al. |
| 2004/0229897 A1 | 11/2004 | Crooks et al. |
| 2005/0054590 A1 | 3/2005 | Averett |
| 2005/0119273 A1 | 6/2005 | Lipford et al. |
| 2006/0052403 A1 | 3/2006 | Isobe et al. |
| 2006/0252774 A1 | 11/2006 | Vatner |
| 2006/0264448 A1 | 11/2006 | Pryde |
| 2007/0037832 A1 | 2/2007 | Isobe et al. |
| 2007/0190071 A1 | 8/2007 | Kurimoto et al. |
| 2007/0197478 A1 | 8/2007 | Jones et al. |
| 2007/0225303 A1 | 9/2007 | Ogita et al. |
| 2007/0249638 A1 | 10/2007 | Giorgio et al. |
| 2008/0008682 A1 | 1/2008 | Chong et al. |
| 2008/0269240 A1 | 10/2008 | Hashimoto et al. |
| 2008/0300244 A1 | 12/2008 | Bonnert et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0209524 A1 | 8/2009 | Bennett et al. |
| 2009/0281075 A1 | 11/2009 | Roughton et al. |
| 2009/0324551 A1 | 12/2009 | Carson et al. |
| 2009/0325877 A1 | 12/2009 | Grunt et al. |
| 2010/0075995 A1 | 3/2010 | Biggadike et al. |
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0240623 A1 | 9/2010 | Cook et al. |
| 2010/0256118 A1 | 10/2010 | Isobe et al. |
| 2010/0280001 A1 | 11/2010 | Bonnert et al. |
| 2010/0298364 A1 | 11/2010 | Bennett et al. |
| 2011/0028715 A1 | 2/2011 | Isobe et al. |
| 2011/0046369 A1 | 2/2011 | Hashimoto et al. |
| 2011/0054168 A1 | 3/2011 | Kurimoto et al. |
| 2011/0136801 A1 | 6/2011 | Isobe et al. |
| 2011/0294802 A1 | 12/2011 | Mcinally et al. |

FOREIGN PATENT DOCUMENTS

| | | |
|---|---|---|
| EP | 1035123 A | 9/2000 |
| EP | 1043021 A1 | 10/2000 |
| EP | 1147108 B1 | 8/2003 |
| EP | 1386923 A1 | 2/2004 |
| EP | 1550662 A1 | 7/2005 |
| EP | 1220862 B2 | 3/2006 |
| EP | 1728793 A1 | 12/2006 |
| EP | 1908480 A1 | 4/2008 |
| EP | 1939198 A1 | 7/2008 |
| EP | 1939201 A1 | 7/2008 |
| EP | 1939202 A1 | 7/2008 |
| EP | 2138497 A1 | 12/2009 |
| EP | 2246353 A1 | 11/2010 |
| GB | 1375162 | 11/1974 |
| JP | 10-501533 A | 2/1988 |
| JP | 08-165292 A | 6/1996 |
| JP | 9-347422 | 11/1997 |
| JP | 9-367449 | 12/1997 |
| JP | 9-367451 | 12/1997 |
| JP | 10-507171 A | 7/1998 |
| JP | 11-180981 A | 7/1999 |
| JP | 11-180982 A | 7/1999 |
| JP | 11-193282 A | 7/1999 |
| JP | 2000-159767 A | 6/2000 |
| JP | 2003-511460 A | 3/2003 |
| JP | 2004-137157 A | 5/2004 |
| JP | 2005-089334 A | 4/2005 |
| JP | 2007-504232 A | 3/2007 |
| WO | WO 95/35297 A1 | 12/1995 |
| WO | WO 96/11200 A1 | 4/1996 |
| WO | WO 98/01448 A1 | 1/1998 |
| WO | WO 99/28321 A1 | 6/1999 |
| WO | WO 99/32122 A1 | 7/1999 |
| WO | WO 99/50249 A2 | 10/1999 |
| WO | WO 00/12487 A1 | 3/2000 |
| WO | WO 00/43394 A1 | 7/2000 |
| WO | WO 00/76519 A1 | 12/2000 |
| WO | WO 01/27131 A1 | 4/2001 |
| WO | WO 02/04448 A2 | 1/2002 |
| WO | WO 02/04449 A2 | 1/2002 |
| WO | WO 02/04450 A2 | 1/2002 |
| WO | WO 02/04451 A2 | 1/2002 |
| WO | WO 02/04452 A2 | 1/2002 |
| WO | WO 02/40481 A2 | 5/2002 |
| WO | WO 02/085905 A1 | 10/2002 |
| WO | WO 03/011864 A1 | 2/2003 |
| WO | WO 2004/011481 A1 | 2/2004 |
| WO | WO 2004/029054 A1 | 4/2004 |
| WO | WO 2004/075865 A2 | 9/2004 |
| WO | WO 2004/087049 A2 | 10/2004 |
| WO | WO 2005/025583 A2 | 3/2005 |
| WO | WO 2005/092892 A1 | 10/2005 |
| WO | WO 2005/092893 A1 | 10/2005 |
| WO | WO 2006/029115 A2 | 3/2006 |
| WO | WO 2006/091394 A2 | 8/2006 |
| WO | WO 2006/117670 A1 | 11/2006 |
| WO | WO 2006/129784 A1 | 12/2006 |
| WO | WO 2007/024707 A2 | 3/2007 |
| WO | WO 2007/031726 A1 | 3/2007 |
| WO | WO 2007/034173 A1 | 3/2007 |
| WO | WO 2007/034817 A1 | 3/2007 |
| WO | WO 2007/034881 A1 | 3/2007 |
| WO | WO 2007/034882 A1 | 3/2007 |
| WO | WO 2007/034916 A1 | 3/2007 |
| WO | WO 2007/034917 A1 | 3/2007 |
| WO | WO 2007/093901 A1 | 8/2007 |
| WO | WO 2008/004948 A1 | 1/2008 |
| WO | WO 2008/005555 A1 | 1/2008 |
| WO | WO 2008/071976 A1 | 6/2008 |
| WO | WO 2008/101867 A1 | 8/2008 |
| WO | WO 2008/114006 A1 | 9/2008 |
| WO | WO 2008/114008 A1 | 9/2008 |
| WO | WO 2008/114817 A1 | 9/2008 |
| WO | WO 2008/114819 A1 | 9/2008 |
| WO | WO 2008/135791 A1 | 11/2008 |
| WO | WO 2009/005687 A1 | 1/2009 |
| WO | WO 2009/034386 A1 | 3/2009 |
| WO | WO 2009/062059 A2 | 5/2009 |
| WO | WO 2009/067081 A1 | 5/2009 |
| WO | WO 2009/078798 A1 | 6/2009 |
| WO | WO 2009/091031 A1 | 7/2009 |
| WO | WO 2009/091032 A1 | 7/2009 |
| WO | WO 2009/151910 A2 | 12/2009 |
| WO | WO 2010/018133 A1 | 2/2010 |
| WO | WO 2010/033074 A1 | 3/2010 |
| WO | WO 2010/133882 A1 | 11/2010 |
| WO | WO 2010/133885 A1 | 11/2010 |

OTHER PUBLICATIONS

Mayo Clinic. "Ovarian Cancer." © 2013. Available from: < http://www.mayoclinic.com/health/ovarian-cancer/DS00293/METHOD=print&DSECTION=all >.*

Navigating Cancer & Blood Disorders. © 2013. Available from: < https://www.navigatingcancer.com/library/all/chemotherapy_drugs >.*

"Asthma" (MDAdvice.com) [online]. http://www.mdadvice.com/topics/asthma/info/1.htm. Downloaded from the internet Oct. 19, 2010.

"Chronic obstructive pulmonary disease"(AllRefer.com Health) [online]. http://health.allrefer.com/health/chronic-obstructive-pulmonary-disease-prevention.html. Downloaded from the internet Oct. 19, 2010.

"Respiratory experts call for global approach to treat chronic diseases" Feb. 13, 2007 [online], http://www.medwire-news.md/48/

(56) References Cited

OTHER PUBLICATIONS

64443/Respiratory/Respiratory_experts_call_for_global_approach_to_treat_chronic_disease.html. Downloaded from the internet Oct. 19, 2010.
Aoki et al, "Weekly Dosing of AZD8848/DSP-3025, a Novel TLR7 Agonist Antedrug, Demonstrates a Prolonged Period of Control Against Markers of Pulmonary Inflammation in an Alergen Challenge Model in the Mouse" Poster presented at the American Thoracic Society International Conference 2010, New Orleans, May 2010, Abstract 529.
Balchen, T. et al., "Pharmacokinetics, safety and tolerability of single ascending intranasal doses of AZD8848 in BChE-deficient volunteers" Poster presented at the American Thoracic Society International Conference 2012, San Francisco, May 18-23, 2012.
Bell et al "AZD8848/DSP-3025, a Novel Potent TLR7 Agonist Antedrug, Demonstrates Negligible Systemic Activity and a Prolonged Period of Control After Cessation of Weekly Dosing in a Brown Norway Rat Ovalbumin Challenge Model" Poster presented at the American Thoracic Society International Conference 2010, New Orleans, May 2010, Abstract 291.
Biffen, M. et al. "Biological characterization of a novel class of toll-like receptor 7 agonists designed to have reduced systemic activity" *Br J Pharmacol*. May 2012; 166(2):573-86.
Biffen, M. et al. "Novel TLR7 agonists for the treatment of allergic diseases" Toll 2011 Meeting, Riva del Garda, Italy, May 4-7, 2011—abstract.
Biological Activity of a Novel TLR7 Agonist Antedrug for the Treatment of Allergic Diseases; Biffen et al the American Thoracic Society International Conference 2010, New Orleans May 2010—abstract.
Chavarot, M. et al. "Synthesis of an adenine-pyridinaidoxime-acridine conjugate for recognition of abasic site lesions in DNA" *Tetrahedron*. Oct. 6, 1997; 53(40):13749-56.
Drazen, J.M. "Surgery for emphysema—not for everyone" *N Engl J Med*. Oct. 11, 2001; 345(15):1126-28.
Dvořáková, H. et al. "Synthesis of 2'-aminomethyl derivatives of N-(2-(phosphonomethoxy)ethyl) nucleotide analogues as potential antiviral agents" *J Med Chem*. Aug. 16, 1996; 39(17):3263-68.
Eiho K. et al. "Mechanism of long-lasting suppression against Th2 immune response in the lung by a novel antedrug TLR7 agonist" European Respiratory Society, Annual Congress, Amsterdam, Sep. 24-28, 2011. Abstract No. 850399 and poster.
Falco et al., "2,4-Diaminopyrimidines as Antimalarials. I. 5-Aryloxyl and 5-Alkoxyl Derivatives" *J. Am. Chem. Soc*. Aug. 1951; 73(8):3753-58.
Fridkin, S.K. "Vancomycin-intermediate and -resistant *Staphylococcus aureus*: What the infectious disease specialist needs to know" *Clin Infect Dis*, Jan. 2001; 32(1):108-15. Epub Dec. 13, 2000.
Greiff, L. et al. "Efficacy and tolerability of the Toll-like receptor 7 agonist AZD8848 in patients with seasonal allergic rhinitis" Abstract, The American Thoracic Society International Conference 2012, San Francisco, May 18-23, 2012.
Greiff, L. et al. "Repeated intranasal TLR7 stimulation reduces allergen responsiveness in allergic rhinitis" *Respir Res*. Jun. 22, 2012; 13(1):53 (10 pages).
Greiff, L. et al. "Repeated intranasal TLR7 stimulation reduces allergen responsiveness in allergic rhinitis" European Respiratory Society, Annual Congress, 2011, Amsterdam, Sep. 24-28, 2011. Abstract No. 854629.
Hirota, K et al., "Discovery of 8-hydroxyadenines as a novel type of interferon inducer" *J. Med. Chem*. 2002; 45(25).5419-22.
Holy, A. et al. "Studies on S-adenosyl-L-homocysteine hydrolase. XVI. 9-(Aminoalkyl)-8-hydroxyadenines: preparation mechanism of formation, and use in affinity chromatography of S-adenosyl-L-homocysteine hydrolase" *Collection of Czechoslovak Chemical Communications*. 1986; 51(2):459-77.
Identification and pharmacology of novel TLR7 agonist antedrugs; RSC BMSC Inflammation meeting Nov. 18, 2010 by Tom McInally.
Ikeda, K. et al. "AZD8848/DSP-3025, A Novel Potent TLR7 Agonist Antedrug, Demonstrates Efficacy against Airway Obstruction and Other Inflammatory Endpoints in Guinea Pig Models of Rhinitis and Asthma with Acute and Weekly Dosing" Poster presented at the American Thoracic Society International Conference 2010, New Orleans, May 2010, Abstract 786.
Isobe, Y et al. "Synthesis and biological evaluation of novel 9-substituted-8-hydroxyadenine derivatives as potent interferon inducers" *J Med Chem*. Mar. 23, 2006; 49(6):2088-95.
Isobe, Y. et al., "Synthesis and structure-activity relationships of 2-substituted-8-hydroxyadenine derivatives as orally available interferon inducers without emetic side effects" *Bioorg Med Chem*. Aug. 15, 2003; 11(17):3641-47.
Itahara, T. et al. "Control of liquid-crystalline properties by base pairing of adenine and thymine" *ChemPhysChem*. 2002; 3(4):378-9.
Korc, M. "Pathways for aberrant angiogenesis in pancreatic cancer" *Molecular Cancer*. 2003; 2(8).
Krueger, R.F. et al., "Tilorone hydrochloride: an orally active antiviral agent" *Science*. Sep. 18, 1970; 169(3951):1213-4.
Kühn, W. et al. "Impact of dose and dosing frequency of intranasal AZD8848 (a TLR7 agonist) on biomarker response in healthy volunteers" Poster presented at the American Thoracic Society International Conference 2012, San Francisco, May 18-23, 2012.
Kurimoto, A. et al. "Synthesis and biological evaluation of 8-oxoadenine derivatives as Toll-like Receptor 7 agonists introducing the antedrug concept" *J. Med Chem*. 2010; 53:2964-72.
Kurimoto, A. et al., "Prodrugs of 9-benzyl-8-hydroxy-2-(2-hydroxyethylthio)adenine: potent interferon inducing agents in monkeys" *Chem Pharm Bull (Tokyo)*; Apr. 2004; 52(4):466-69.
Kurimoto, A. et al., "Synthesis and evaluation of 2-substituted 8-hydroxyadenines as potent interferon inducers with improved oral bioavailabilities" *Bioorg Med Chem*. Mar. 1, 2004; 12(5):1091-99.
Kurimoto, A. et al., "Synthesis and structure-activity relationships of 2-amino-8-hydroxyadenines as orally active interferon inducing agents" *Bioorg Med Chem*. Dec. 1, 2003; 11(24):5501-8.
Laino, C. "In Small Study, Imaging Detects Lung Damage in People Exposed to Secondhand Smoke" *Oncology Times*. Jan. 25, 2008; 30(2):15.
Leaker, B. et al. "Effects of the novel Toll-like receptor 7 (TLR7) agonist AZD8848 on allergen-induced responses in patients with mild asthma" Presented at the European Respiratory Society Annual Congress, Vienna, Sep. 1-5, 2012.
Leaker, B. et al. "The effects of the novel Toll-like receptor 7 (TLR7) agonist AZD8848 on allergen-induced responses in patients with mild asthma" Poster presented at the American Thoracic Society International Conference 2012, San Francisco, May 18-23, 2012.
Lee, J. et al, "Activation of anti-hepatitis C virus responses via Toll-like receptor 7" *Proc Natl Acad Sci USA*. Feb. 7, 2006; 103(6):1828-33.
Lee, J. et al. "Molecular basis for the immunostimulatory activity of guanine nucleoside analogs: activation of Toll-like receptor 7" *Proc Natl Acad Sci USA*. May 27, 2003; 100(11):6646-51. Epub May 8, 2003.
Matsui, H. et al. "Mechanism of action of inhibition of allergic immune responses by a novel antedrug TLR7 agonist" *J Immunol*. Dec. 1, 2012;189(11):5194-205.
Mayer, G.D. et al. "Tilorone hydrochloride: mode of action" *Science*. Sep. 18, 1970; 169(3951):1214-5.
McInally, T. et al. "Identification of a Novel Tlr7 Agonist Antedrug" Poster presented at EFMC-ISMC 2010, Brussels, Belgium, Sep. 5-9, 2010.
Mechanisms of Inhibition of Type-2 Cytokines by Novel TLR7 Agonist Antedrugs, Matsui et al, the American Thoracic Society International Conference 2010, New Orleans May 2010.
Mogulkoc, N. et al. "Pulmonary function in idiopathic pulmonary fibrosis and referral for lung transplantation" *Am J Respir Crit Care Med*. Jul. 1, 2001; 164(1):103-8.
Nichol, F.R. et al. "Stimulation of murine interferon by a substituted pyrimidine" *Antimicrob Agents Chemother*. Mar. 1976; 9(3):433-9.
Palmer, S. et al. "Highly drug-resistant HIV-1 clinical isolates are cross-resistant to many antiretroviral compounds in current clinical development" *AIDS*. Apr. 16, 1999; 13(6):661-7.
Reiter, M.J. et al. "Cytokine induction in mice by the immunomodulator imiquimod" *J Leukoc Biol*. Feb. 1994; 55(2):234-40.

(56) References Cited

OTHER PUBLICATIONS

Spassova, M. et al. "Synthesis of N-(3-Azido-2-hydroxypropyl), N-(3-Phthalimido-2-hydroxypropyl) and N-(3-Amino-2-hydroxypropyl) Derivatives of Heterocyclic Bases" *Collect. Czech. Chem. Commun.* 1994; 59:1153-74.

Stringfellow, D.A. et al. "Antiviral and interferon-inducing properties of 1,5-diamino anthraquinones" *Antimicrob Agents Chemother.* Jan. 1979; 15(1):111-8.

Tarköy et al. "Nucleic-Acid Analogues with Constraint Conformational Flexibility in the Sugar-Phosphate Backbone ('Bicyclo-DNA'). Part 1. Preparation of (3'S,5'R)-2'-Deoxy-3',5'-ethano-αβ-D-ribonucleosides ('Bicyclonucleosides')" *Helvetica Chimica Acta.* 1993; 76(1):481-510.

Tojo et al. "Synthesis and Biological Evaluation of a Novel Tlr7 Agonist with an Antedrug Strategy" Poster presented at EFMC-ISMC 2010, Brussels, Belgium, Sep. 5-9, 2010.

U.S. Appl. No. 60/937,726, filed Jun. 29, 2007, by Halcomb, entitled "TRL-7 Agonists.".

U.S. Appl. No. 60/959,714, filed Jul. 16, 2007, by Graupe et al., entitled "Modulators of Toll-Like Receptor 7.".

Yoshimoto et al., "Correlation Analysis of Baker's Studies on Enzyme Inhibition. 2. Chymotrypsin, Trypsin, Thymidine Phosphorylase, Uridine Phosphorylase, Thymidylate Synthetase, Cytosine Nucleoside Deaminase, Dihydrofolate Reductase, Malate Dehydrogenase, Glutamate Dehydrogenase, Lactate Dehydrogenase, and Glyceraldehyde-phosphate Dehydrogenase" *J. Med. Chem.* Jan. 1976; 19(1):71-98.

Zalutsky, M.R. "Targeted radiotherapy of brain tumours" *Br J Cancer.* Apr. 19, 2004; 90(8):1469-73.

\* cited by examiner

X-ray powder diffractogram of Form A

Differential Scanning Calorimetry (DSC) trace for Form A

X-ray powder diffractogram of Form B

Differential Scanning Calorimetry (DSC) trace for Form B

X-ray powder diffractogram of Form C

Differential Scanning Calorimetry (DSC) trace for Form C

PURINE DERIVATIVES

The present invention relates to the compound methyl [4-({[3-(6-amino-2-butoxy-8-oxo-7,8-dihydro-9H-purin-9-yl)propyl][3-(piperidin-1-yl)propyl]amino}methyl)phenyl]acetate and pharmaceutically acceptable salts thereof, pharmaceutical compositions containing the compound and its use in therapy.

The immune system is comprised of innate and acquired immunity, both of which work cooperatively to protect the host from microbial infections. It has been shown that innate immunity can recognize conserved pathogen-associated molecular patterns through toll-like receptors (TLRs) expressed on the cell surface of immune cells. Recognition of invading pathogens then triggers cytokine production (including interferon alpha (IFNα)) and upregulation of co-stimulatory molecules on phagocytes, leading to modulation of T cell function. Thus, innate immunity is closely linked to acquired immunity and can influence the development and regulation of an acquired response.

TLRs are a family of type I transmembrane receptors characterized by an $NH_2$-terminal extracellular leucine-rich repeat domain (LRR) and a COOH-terminal intracellular tail containing a conserved region called the Toll/IL-1 receptor (TIR) homology domain. The extracellular domain contains a varying number of LRR, which are thought to be involved in ligand binding. Eleven TLRs have been described to date in humans and mice. They differ from each other in ligand specificities, expression patterns, and in the target genes they can induce.

Ligands which act via TLRs (also known as immune response modifiers (IRMS)) have been developed, for example, the imidazoquinoline derivatives described in U.S. Pat. No. 4,689,338 which include the product Imiquimod for treating genital warts, and the adenine derivatives described in WO 98/01448 and WO 99/28321.

TLR7 agonists suppress the Th2 cell dependent immune response through enhancement of the Th1 response. Such agonists are expected to be useful in the treatment of a number of diseases by modulating the Th1/Th2 immune response. However, systemic exposure to a TLR7 agonist may result is undesirable side-effects such as flu-like symptoms caused by induction of cytokines including IL-6, IL-12, and type I IFN.

WO2005/0092893 describes a class of 9-substituted oxoadenine derivatives having immuno-modulating properties that act via TLR7 which are useful in the treatment of, for example, viral or allergic diseases, skin conditions such as atopic dermatitis and cancers. The ester moieties in the compounds described in WO2005/0092893 are quickly metabolised in plasma to the less active acid. The compounds are therefore suitable for topical administration and are expected to exert the desired effects at the site of administration, but be quickly converted to the less active acid metabolite upon entry into the systemic circulation, thereby reducing undesirable side effect which may be associated with systemic exposure to a TLR7 agonist.

Following administration of a drug, elimination from the body occurs either by metabolism, usually by the liver or gut mucosa, or by excretion, usually by the kidneys and/or liver. Hepatic metabolism occurs primarily by the cytochrome P450 family (CYP) of enzymes located in the hepatic endoplasmic reticulum. The Cytochrome P450's are a large family of isoenzymes which has been categorized into over 15 subfamilies. The CYP3A subfamily, which includes CYP3A4, 3A5, 3A7 and 3A4 is responsible for the metabolism of about 60% of known therapeutic drugs. CYP3A4 in particular is the most abundant CYP isoenzyme in both liver and intestine and is involved in the metabolism of more than 50% of the clinically used drugs (Mechanism-Based Inhibition of Cytochrome P455 3A4 by Therapeutic Drugs. Clin. Pharmacokinet, 2005, 44, 279-304). Like all other CYP enzymes, CYP3A4 is susceptible to both reversible and irreversible or mechanism based inhibition (Time-dependent CYP Inhibition. Expert Opin. Drug Metab. Toxicol. 2007, 3, 51-66). Their low substrate specificity makes the CYP enzymes susceptible to inhibition by a wide variety of structurally distinct drugs.

If a CYP inhibitor is co-administered with another agent which is metabolised by that particular CYP, the CYP inhibitor can result in significant increases in the blood and tissue concentrations of the other agent. Such changes can alter the safety and efficacy profile, especially in drugs with narrow therapeutic windows. Therefore, it is generally desirable to find drugs which have a low CYP inhibition, particularly of CYP3A4, to minimise the possibility of adverse drug-drug interactions.

It has now surprisingly been found the compound methyl [4-({[3-(6-amino-2-butoxy-8-oxo-7,8-dihydro-9H-purin-9-yl)propyl][3-(piperidin-1-yl)propyl]amino}methyl)phenyl] acetate and pharmaceutically acceptable salts thereof is a potent TLR7 agonist with a favourable CYP profile, exhibiting low CYP3A4 inhibition. In addition, the compound has a number of other favourable properties including one or more of; a short half-life in plasma (for example human plasma); a high ratio of ester to acid activity. The compound exhibits favourable skin permeability, in particular good penetration through the stratum corneum and as such is expected to be useful for the treatment of conditions by dermal application. Accordingly, the compound is expected to be suitable as a TLR7 agonist useful in the treatment of a number of conditions discussed hereinafter, for example by topical application of the compound.

The structure of methyl [4-({[3-(6-amino-2-butoxy-8-oxo-7,8-dihydro-9H-purin-9-yl)propyl][3-(piperidin-1-yl)propyl]amino}methyl)phenyl]acetate (hereafter "Compound (I)") is shown below:

Compound (I)

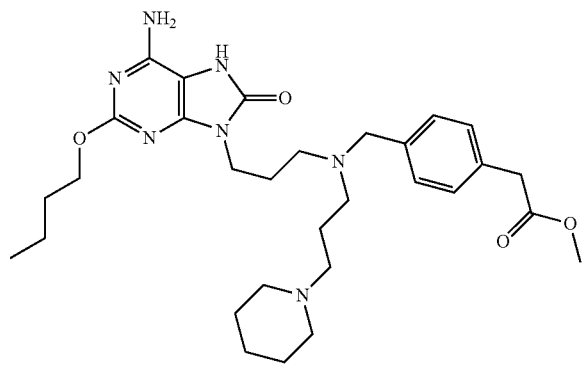

Thus, in accordance with the present invention, there is provided Compound (I), or a pharmaceutically acceptable salt thereof.

Compound (I), or a pharmaceutically acceptable salt thereof, may exist in tautomeric forms. It is to be understood that all tautomers and mixtures thereof are included within the scope of the invention, including the hydroxy tautomer of the formula:

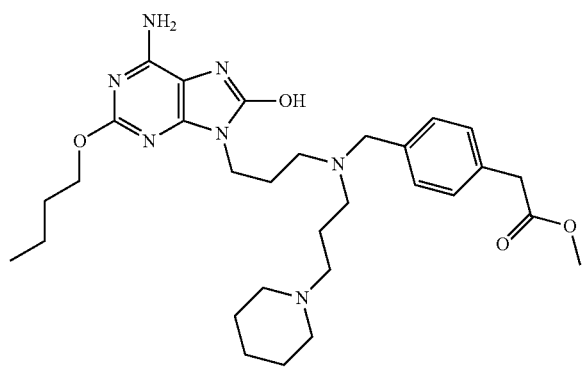 [SMILES: CCCCOc1nc(N)c2nc(O)n(CCCN(CCCN3CCCCC3)Cc3ccc(CC(=O)OC)cc3)c2n1]

It is to be understood that Compound (I), or a pharmaceutically acceptable salt thereof, may exist in solvated as well as unsolvated forms such as, for example, hydrated forms. It is to be understood that the invention encompasses all such solvated forms.

It is also to be understood that Compound (I), or a pharmaceutically acceptable salt thereof, may exhibit polymorphism, and that the invention encompasses all such forms.

A suitable pharmaceutically acceptable salt of Compound (I) is, for example, an acid-addition salt of Compound (I), for example an acid-addition salt with an inorganic or organic acid. Examples of inorganic acid addition salts include hydrochloride, hydrobromide, sulfate, hydroiodide, nitrate and phosphate. Examples of organic acid salts include citrate, oxalate, acetate, formate, propionate, benzoate, trifluoroacetate, maleate, tartrate, methanesulfonate, benzenesulfonate and p-toluenesulfonate. Particular salts of Compound (I) include the hydrochloride, formate or hydrobromide salts. In one embodiment of the invention there is provided a hydrochloride salt of Compound (I). In another embodiment of the invention there is provided a hydrobromide salt of Compound (I).

In the context of the present invention, the term "salt" defines a crystalline material in which the Compound (I) and the acid are ionized or alternatively, where both components utilise prominent intermolecular interactions, such as hydrogen bonding, to combine and yield a uniform crystalline material (a co-crystal). It will be appreciated that a salt according to the invention may be partially ionic and partially co-crystal.

A further aspect of the invention provides a crystalline form of Compound (I), hereafter Form A. Form A is crystalline and provides an X-ray powder diffraction pattern substantially as shown in FIG. 1 when measured at a wavelength of 1.5418 Å. The most prominent peaks (2θ values) of the XRPD pattern for Form A are shown in Table 1. The 2θ values in Table 1 are measured to an accuracy of +/−0.1°.

TABLE 1

| Angle 2-Theta (2θ)° |
|---|
| 3.0 (w) |
| 5.9 (vs) |
| 8.8 (vs) |
| 11.8 (w) |
| 17.7 (w) |
| 18.2 (w) |
| 21.0 (w) |

Form A further provides a characteristic differential scanning calorimetry curve, at a linear heating rate of 10° C. per minute in an aluminium sample pan under a nitrogen atmosphere, exhibiting an endothermic transition with an onset temperature of 125(±3)° C. and a second endothermic transition with an onset temperature of 164(±3)° C.

Form A may be prepared as described in Example 1 hereinafter.

Accordingly, in one embodiment of the invention there is provided Form A, characterised in that said Form A has an X-ray powder diffraction pattern with at least one specific peak at a 2θ value selected from Table 1 +/−0.1°, when measured at a wavelength of 1.5418 Å.

According to another embodiment of the invention there is provided Form A, characterised in that said Form A has an X-ray powder diffraction pattern with at least two specific peaks (for example at least 2, 3, 4, 5, 6 or 7 peaks) at 2θ values selected from Table 1 +/−0.1°, when measured at a wavelength of 1.5418 Å.

According to another embodiment of the invention there is provided Form A, characterised in that said Form A has an X-ray powder diffraction pattern substantially as shown in FIG. 1.

According to another embodiment of the invention there is provided Form A, characterised by the differential scanning calorimetry curve substantially as shown in FIG. 2.

A still further aspect of the invention provides a crystalline form of the hydrochloride salt of Compound (I), hereafter Form B. Form B is crystalline and provides an X-ray powder diffraction pattern substantially as shown in FIG. 3 when measured at a wavelength of 1.5418 Å. The most prominent peaks (2θ values) of the XRPD pattern for Form B are shown in Table 2. The 2θ values in Table 2 are measured to an accuracy of +/−0.1°.

TABLE 2

| Angle 2-Theta (2θ)° |
|---|
| 7.3 (s) |
| 9.7 (s) |
| 11.0 (vs) |
| 12.9 (m) |
| 14.3 (w) |
| 18.4 (s) |
| 21.2 (m) |

Form B further provides a characteristic differential scanning calorimetry curve, at a linear heating rate of 10° C. per minute in an aluminium sample pan under a nitrogen atmosphere, exhibiting an endothermic transition with an onset temperature of 131(±3)° C.

Form B may be prepared as described in Example 2 hereinafter.

Accordingly, in one embodiment of the invention there is provided Form B, characterised in that said Form B has an X-ray powder diffraction pattern with at least one specific peak at a 2θ value selected from Table 2 +/−0.1°, when measured at a wavelength of 1.5418 Å.

According to another embodiment of the invention there is provided Form B, characterised in that said Form B has an X-ray powder diffraction pattern with at least two specific peaks (for example at least 2, 3, 4, 5, 6 or 7 peaks) at 2θ values selected from Table 2 +/−0.1°, when measured at a wavelength of 1.5418 Å.

According to another embodiment of the invention there is provided Form B, characterised in that said Form B has an X-ray powder diffraction pattern substantially as shown in FIG. 3.

According to another embodiment of the invention there is provided Form B, characterised by the differential scanning calorimetry curve substantially as shown in FIG. 4.

A yet further aspect of the invention provides a crystalline form of the hydrobromide salt of Compound (I), hereafter Form C. Form C is crystalline and provides an X-ray powder diffraction pattern substantially as shown in FIG. 5 when measured at a wavelength of 1.5418 Å. The most prominent peaks (2θ values) of the XRPD pattern for Form C are shown in Table 3. The 2θ values in Table 3 are measured to an accuracy of +/−0.1°.

TABLE 3

| Angle 2-Theta (2θ)° |
|---|
| 7.4 (m) |
| 9.5 (w) |
| 11.2 (vs) |
| 19.4 (m) |
| 20.3 (w) |
| 21.4 (m) |
| 22.5 (m) |

Form C further provides a characteristic differential scanning calorimetry curve, at a linear heating rate of 10° C. per minute in an aluminium sample pan under a nitrogen atmosphere, exhibiting an endothermic transition with an onset temperature of 121(±3)° C.

Form C may be prepared as described in Example 3 hereinafter.

Accordingly, in one embodiment of the invention there is provided Form C, characterised in that said Form C has an X-ray powder diffraction pattern with at least one specific peak at a 2θ value selected from Table 3 +/−0.1°, when measured at a wavelength of 1.5418 Å.

According to another embodiment of the invention there is provided Form C, characterised in that said Form C has an X-ray powder diffraction pattern with at least two specific peaks (for example at least 2, 3, 4, 5, 6 or 7 peaks) at 2θ values selected from Table 3 +/−0.1°, when measured at a wavelength of 1.5418 Å.

According to another embodiment of the invention there is provided Form C, characterised in that said Form C has an X-ray powder diffraction pattern substantially as shown in FIG. 5.

According to another embodiment of the invention there is provided Form C, characterised by the differential scanning calorimetry curve substantially as shown in FIG. 6.

Compound (I) may be prepared using analogous methods to those described WO2005/0092893 or EP2246353 and as illustrated Examples herein.

A further aspect of the present invention provides a process for the preparation of a Compound (I), or a pharmaceutically acceptable salt thereof comprising:

Process (a)

The reaction of a compound of the formula (II), or a salt thereof:

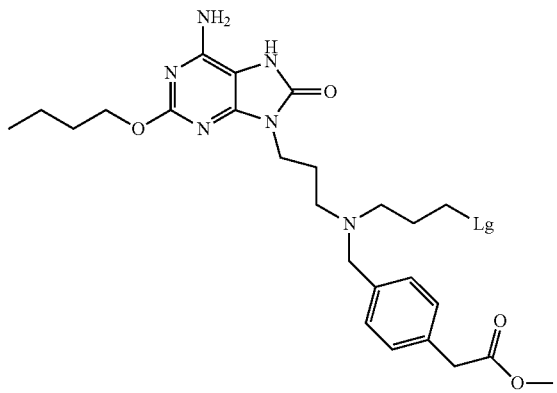

(II)

wherein Lg is a leaving group;
with piperidine; or

Process (b)

The reaction of a compound of the formula (III), or a salt thereof:

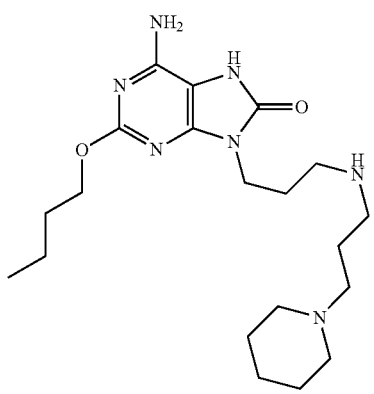

(III)

with methyl (4-formylphenyl)acetate in the presence of a reducing agent;
and thereafter optionally forming a pharmaceutically acceptable salt of Compound (I).

Process (a) Conditions

Examples of leaving groups represented by Lg in the compound of formula (II) include halo (for example chloro, bromo or iodo), mesylate (methylsulfonyloxy) triflate (trifluoromethanesulfonyloxy), besylate (benzenesulfonyloxy) or tosylate (toluenesulfonyloxy).

The reaction is suitably carried out in the presence of a solvent for example a polar aprotic solvent such as tetrahydrofuran, dichloromethane, dimethylformamide or dimethylsulfoxide or an non-polar organic solvent such as toluene. The reaction temperature is suitably performed at a temperature in the range of room temperature to the reflux temperature of the reaction mixture.

The compound of formula (II) may be prepared by for example, reaction of a compound of formula (IV), or a salt thereof:

(IV)

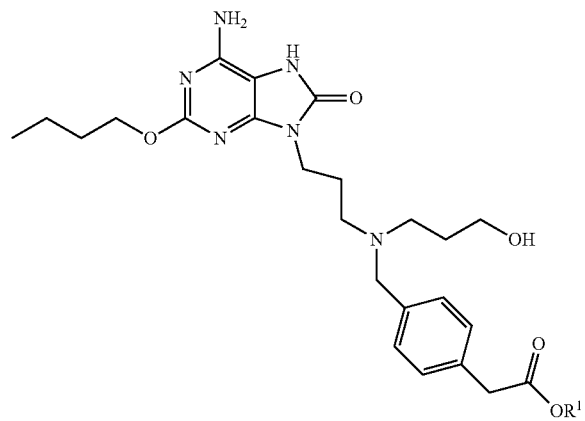

wherein R[1] is hydrogen or methyl;
with a suitable precursor of the leaving group Lg. For example, when Lg is mesylate by reaction with methanesulfonyl chloride. When Lg is chloro, the compound of formula (IV) may be reacted with a suitable chlorinating agent such as thionyl chloride. When Lg is iodo, a compound of formula (II) wherein Lg is chloro may be reacted with sodium iodide.

When R[1] is hydrogen in the compound of formula (IV), the acid may be converted to the methyl ester by reaction with methanol using well known conditions as described in the examples herein.

Compounds of formula (IV) may be prepared as described herein in the Examples.

Process (b) Conditions

Process (b) is carried by reaction of compound of the formula (III), or a salt thereof and methyl (4-formylphenyl) acetate under reductive amination conditions in the presence of a suitable reducing agent. Examples of reducing agents, include a hydride reducing agent, for example an alkali metal aluminium hydride such as lithium aluminium hydride, or, suitably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran or diethyl ether for the more powerful reducing agents such as lithium aluminium hydride, and, for example, methylene chloride or aprotic solvent such as methanol and ethanol for the less powerful reducing agents such as sodium triacetoxyborohydride and sodium cyanoborohydride. A particular reducing agent is sodium triacetoxyborohydride. The reaction is performed at a temperature in the range, for example, 0 to 100° C., such as 0 to 40° C. or, conveniently, at or near ambient temperature. The reaction may optionally be carried out in the presence of an base, such as an organic base, for example triethylamine.

Suitably the compound of formula (III) is used in the form of a salt, for example a hydrochloride, hydrobromide, maleate, fumarate, malonate, oxalate, trifluoroacetate. Particular salts of the compound of formula (III) include a hydrochloride, maleate, fumarate, or malonate, more particularly the dimaleate salt.

Optionally the reaction may be carried out in the presence of a base, for example an tertiary amine base such as tertiary amine such as triethylamine, diisopropylethylamine, N-methylmorpholine or 4-(N,N-dimethylamino)pyridine. A particular base is triethylamine.

The compound of formula (III) may be prepared by, for example the method described in Reaction Scheme 1:

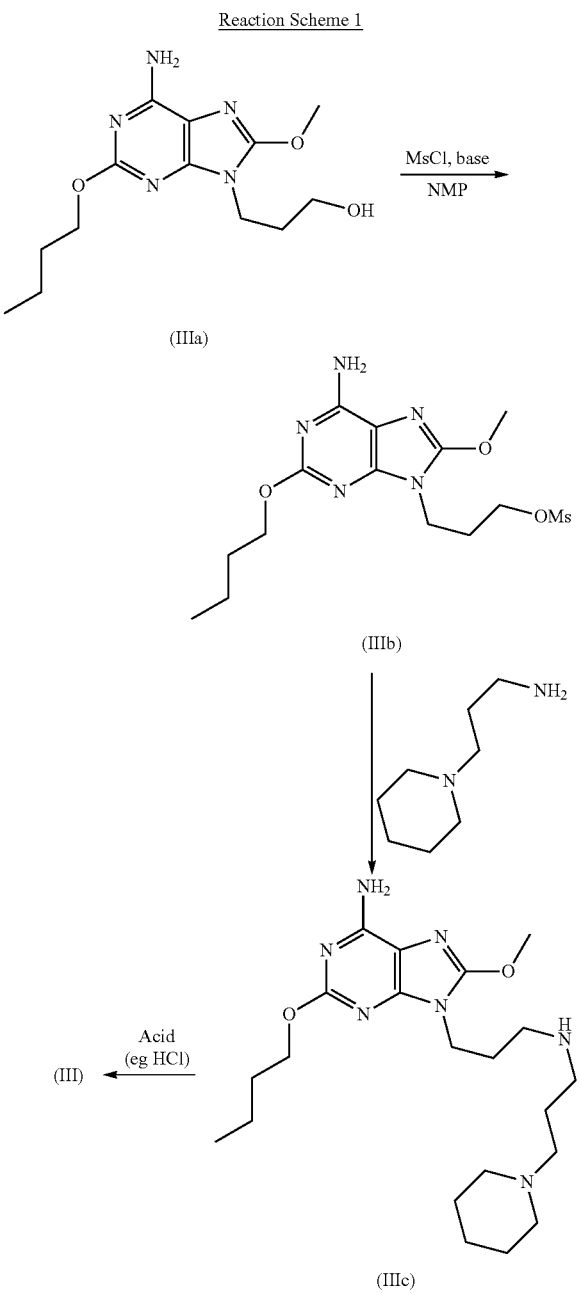 [SMILES: CCCCOc1nc(N)c2nc(OC)n(CCCO)c2n1 ; CCCCOc1nc(N)c2nc(OC)n(CCCOS(C)(=O)=O)c2n1 ; NCCCN1CCCCC1 ; "(III)" ; CCCCOc1nc(N)c2nc(OC)n(CCCNCCCN3CCCCC3)c2n1]

Suitable conditions for Reaction Scheme 1 are analogous to those described in EP2246353 and as specifically illustrated in the Examples herein. In Reaction Scheme 1 the reaction of the Compound (IIIc) with an acid such as hydrochloric acid provides Compound (III) in the form of a salt. We have found that conversion of Compound (III) to the free base and recrystallisation as a salt such as the dimaleate salt provides a salt of compound (III) in high purity, which is particularly suitable for use in Process (b).

It will be appreciated by those skilled in the art that in the processes of the present invention certain functional groups such as hydroxyl or amino groups in the reagents may need to be protected by protecting groups. Thus, the preparation of Compound (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The removal of any protecting groups and the formation of a pharmaceutically acceptable salt of Compound (I) are within the skill of an ordinary organic chemist using standard techniques. For example salts Compound (I) may be prepared by reacting Compound (I) with a suitable acid. Alternatively, using well-known counter ion exchange methods may be used to convert one salt to another.

Certain intermediates used in the preparation of Compound (I) are novel including compounds of the formulae (II), (III) and (IV) or a salt thereof. Such intermediates form a further aspect of the present invention.

According to another aspect of the invention there is provided a compound of the formula (II), or a salt thereof as hereinbefore defined. For example methyl {4-[([3-(6-amino-2-butoxy-8-oxo-7,8-dihydro-9H-purin-9-yl)propyl]{3-[(methylsulfonyl)oxy]propyl}amino)methyl]phenyl}acetate, or a salt thereof.

According to another aspect of the invention there is provided a compound of the formula (III), or a salt thereof as hereinbefore defined. For example, 6-amino-2-butoxy-9-{3-[(3-piperidin-1-ylpropyl)amino]propyl}-7,9-dihydro-8H-purin-8-one, or a salt thereof, for example the dimaleate salt.

According to another aspect of the invention there is provided a compound of the formula (IV), or a salt thereof as hereinbefore defined. For example a compound selected from:

[4-({[3-(6-amino-2-butoxy-8-oxo-7,8-dihydro-9H-purin-9-yl)propyl](3-hydroxypropyl)amino}methyl)phenyl]acetic acid; and
Methyl [4-({[3-(6-amino-2-butoxy-8-oxo-7,8-dihydro-9H-purin-9-yl)propyl](3-hydroxypropyl)amino}methyl)phenyl]acetate;
or a salt thereof.

The intermediates described herein may be used in the form of a salt. The salt may be a pharmaceutically acceptable salt, such as one of the salts mentioned hereinbefore in relation to Compound (I). Alternatively, if required, the intermediates may be used in the form of a salt which is not a pharmaceutically acceptable salt. Such salts may be advantageously used in the synthesis of compounds according to the invention, for example as a result of advantageous physical and/or chemical properties, such as crystallinity.

Diseases and Medical Conditions

Compound (I), or a pharmaceutically acceptable salt thereof, according to the invention is useful as a modulator of TLR7 activity and is expected to provide an immuno-modulator effect and thus be useful as a therapeutic and prophylactic agent for diseases associated with an abnormal immune response (e.g. autoimmune diseases and allergic diseases) and various infections and cancers which are required for activation of an immune response. Compound (I), or a pharmaceutically acceptable salt thereof may also be useful as a vaccine adjuvant. For example, Compound (I), or a pharmaceutically acceptable salt thereof, may be administered to a mammal, including man, for the treatment of the following conditions or diseases:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;
2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, actinic keratosis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; hemangioma; pre-cancerous skin lesions; basal cell carcinoma, for example superficial basal cell carcinoma, nodular basal cell carcinoma and bowen's disease; cutaneous lymphomas, non-melanoma skin cancer and other dysplastic lesions; drug-induced disorders including fixed drug eruptions; skin scarring, including keloids; cutaneous infections, including viral cutaneous infections; and cosmetic effects including photo-damaged skin;
3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;
4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);
5. allograft rejection: acute and chronic following, for example, transplantation of kidney, heart, liver, lung, bone marrow, skin or cornea or following blood transfusion; or chronic graft versus host disease;
6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;
7. oncology: treatment of common cancers including prostate, breast, lung, ovarian, pancreatic, bowel and colon, stomach, skin and brain tumours and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and *mycobacterium avium*, leprosy; other infectious diseases, such as fungal diseases, *chlamydia, candida, aspergillus*, cryptococcal meningitis, *pneumocystis carni*, cryptosporidiosis, histoplasmosis, toxoplasmosis, trypanosome infection and leishmaniasis.

Thus, the present invention provides Compound (I), or a pharmaceutically acceptable salt thereof, for use in therapy.

In a further aspect, the present invention provides the use of Compound (I), or a pharmaceutically acceptable salt thereof, in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, Compound (I), or a pharmaceutically acceptable salt thereof according to the invention may be used in the treatment of asthma, COPD, allergic rhinitis, allergic conjunctivitis, cancer, hepatitis B, hepatitis C, HIV, HPV, bacterial infections or a skin condition as listed hereinbefore (for example, atopic dermatitis, actinic keratosis, pre-cancerous skin lesions or cutaneous vial infections). Compound (I), or a pharmaceutically acceptable salt thereof, may also be useful as a vaccine adjuvant.

Accordingly, as a further aspect of the invention there is provided Compound (I), or a pharmaceutically acceptable salt thereof, for use in the treatment of asthma, COPD or allergic rhinitis.

As a further aspect of the invention there is provided Compound (I), or a pharmaceutically acceptable salt thereof, for use in the treatment of asthma.

As a further aspect of the invention there is provided Compound (I), or a pharmaceutically acceptable salt thereof, for use in the treatment of COPD.

As a further aspect of the invention there is provided Compound (I), or a pharmaceutically acceptable salt thereof, for use in the treatment of allergic rhinitis.

As a further aspect of the invention there is provided Compound (I), or a pharmaceutically acceptable salt thereof, for use as a vaccine adjuvant.

As a further aspect of the invention there is provided Compound (I), or a pharmaceutically acceptable salt thereof, for use in the treatment of a skin condition as hereinbefore described (for example atopic dermatitis, actinic keratosis, pre-cancerous lesions or cutaneous vial infections).

As a further aspect of the invention there is provided the use of Compound (I), or a pharmaceutically acceptable salt thereof, in the manufacture of a medicament for the treatment of asthma, COPD or allergic rhinitis.

As a further aspect of the invention there is provided the use of Compound (I), or a pharmaceutically acceptable salt thereof, in the manufacture of a medicament for the treatment of asthma.

As a further aspect of the invention there is provided the use of Compound (I), or a pharmaceutically acceptable salt thereof, in the manufacture of a medicament for the treatment of COPD.

As a further aspect of the invention there is provided the use of Compound (I), or a pharmaceutically acceptable salt thereof, in the manufacture of a medicament for the treatment of allergic rhinitis.

As a further aspect of the invention there is provided the use of Compound (I), or a pharmaceutically acceptable salt thereof, in the manufacture of a medicament for the treatment of a skin condition as hereinbefore described (for example atopic dermatitis, actinic keratosis, pre-cancerous lesions or cutaneous vial infections).

As a further aspect of the invention there is provided the use of Compound (I), or a pharmaceutically acceptable salt thereof, as a vaccine adjuvant, in the manufacture of a vaccine for the treatment of a disease or condition.

The invention therefore provides a method of treating an inflammatory disease in a patient suffering from, or at risk of, said disease, which comprises administering to the patient a therapeutically effective amount of Compound (I), or a pharmaceutically acceptable salt thereof.

The invention also provides a method of treating an airways disease, e.g. a reversible obstructive airways disease such as asthma, in a patient suffering from, or at risk of, said disease, which comprises administering to the patient a therapeutically effective amount of Compound (I), or a pharmaceutically acceptable salt thereof.

The invention still further provides a method of treating, or reducing the risk of, a disease or condition comprising or arising from abnormal cell growth (e.g. a cancer), which method comprises administering to a patient in need thereof a therapeutically effective amount of Compound (I), or a pharmaceutically acceptable salt thereof.

The invention still further provides a method of treating, or reducing the risk of, a skin disease or condition as hereinbefore described (for example atopic dermatitis, actinic keratosis, pre-cancerous lesions or cutaneous vial infections), which method comprises administering to a patient in need thereof a therapeutically effective amount of Compound (I), or a pharmaceutically acceptable salt thereof.

The invention still further provides a method of treating, or reducing the risk of, a disease or condition, which method comprises administering to a patient in need thereof a therapeutically effective amount of a vaccine and a salt of Compound (I) defined herein or a solvate of the salt.

The invention still further provides a method of increasing the response to a vaccine in a patient, which method comprises administering to a patient in need thereof a therapeutically effective amount of a vaccine and Compound (I), or a pharmaceutically acceptable salt thereof.

For the above-mentioned therapeutic uses the dosage administered will, of course, vary with the mode of administration, the treatment desired and the disorder indicated. For example, the daily dosage of Compound (I), or a pharmaceutically acceptable salt thereof, if inhaled, may be in the range from 0.05 micrograms per kilogram body weight (μg/kg) to 100 micrograms per kilogram body weight (μg/kg). For example a dose of about 0.1, to 100 μg/kg such as a dose of about 0.1, 0.5, 1, 2, 5, 10, 20, 50 or 100 μg/kg. Alternatively, if Compound (I), or a pharmaceutically acceptable salt thereof, is administered orally, then the daily dosage may be in the range from 0.01 micrograms per kilogram body weight (µg/kg) to 100 milligrams per kilogram body weight (mg/kg).

The dosages mentioned herein refer to the dose of Compound (I) as the free base. Accordingly, the equivalent dose of a particular salt will be higher because of the increased molecular weight of the salt compared to the free base.

The compounds according to the invention may be used on their own but will generally be administered in the form of a pharmaceutical composition in which the Compound (I), or a pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition may comprise from 0.05 to 99% w (percent by weight), more preferably from 0.05 to 80% w, still more preferably from 0.10 to 70% w, and even more preferably from 0.10 to 50% w, of Compound (I), all percentages by weight being based on total composition.

The present invention also provides a pharmaceutical composition comprising Compound (I), or a pharmaceutically acceptable salt thereof, in association with a pharmaceutically acceptable adjuvant, diluent or carrier.

The invention further provides a process for the preparation of a pharmaceutical composition of the invention which comprises mixing Compound (I), or a pharmaceutically acceptable salt thereof, with a pharmaceutically acceptable adjuvant, diluent or carrier.

The pharmaceutical compositions may be administered topically (e.g. to the skin or to the lung and/or airways (by oral or nasal inhalation) administration) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Pharmaceutical Compositions for Administration by Inhalation

In one embodiment of the invention, the pharmaceutical composition is administered by inhalation (oral or nasal).

The Compound (I), or a pharmaceutically acceptable salt thereof, may be administered using a suitable delivery device, for example from a dry powder inhaler, a metered dose inhaler, a nebuliser or a nasal delivery device. Such devices are well known.

In a further embodiment, the pharmaceutical composition is administered by means of a dry powder inhaler (DPI).

The DPI may be "passive" or breath-actuated, or "active" where the powder is dispersed by some mechanism other than the patient's inhalation, for instance, an internal supply of compressed air. At present, three types of passive dry powder inhalers are available: single-dose, multiple unit dose or multidose (reservoir) inhalers. In single-dose devices, individual doses are provided, usually in gelatine capsules, and have to be loaded into the inhaler before use, examples of which include Spinhaler® (Aventis), Rotahaler®(GlaxoSmithKline), Aeroliser™ (Novartis), Inhalator® (Boehringer) and Eclipse (Aventis) devices. Multiple unit dose inhalers contain a number of individually packaged doses, either as multiple gelatine capsules or in blisters, examples of which include Diskhaler® (GlaxoSmithKline), Diskus® (GlaxoSmithKline) and Aerohaler® (Boehringer) devices. In multidose devices, drug is stored in a bulk powder reservoir from which individual doses are metered, examples of which include Turbuhaler® (AstraZeneca), Easyhaler® (Orion), Novolizer® (ASTA Medica), Clickhaler® (Innovata Biomed) and Pulvinal® (Chiesi) devices.

An inhalable pharmaceutical composition or dry powder formulation for use in a DPI can be prepared by mixing finely divided active ingredient (having a mass median diameter generally equal to or less than 10 µm, preferably equal to or less than 5 µm) with a carrier substance, for example, a mono-, di- or polysaccharide, a sugar alcohol, or another polyol. Suitable carriers are sugars or sugar alcohols, for example, lactose, glucose, raffinose, melezitose, lactitol, maltitol, trehalose, sucrose, mannitol; and starch. The carrier particles may have a mass median diameter of from 20 to 1000 µm, more usually from 50 to 500 µm. The powder mixture may then, as required, be dispensed into hard gelatine capsules, each containing the desired dose of the active ingredient.

Alternatively, an inhalable pharmaceutical composition may be prepared by processing a finely divided powder (e.g. consisting of finely divided active ingredient and finely divided carrier particles) into spheres that break up during the inhalation procedure. This spheronized powder is filled into the drug reservoir of a multidose inhaler, for example, that known as the Turbuhaler® in which a dosing unit meters the desired dose which is then inhaled by the patient.

Accordingly, the present invention also provides a dry powder inhaler, in particular a multiple unit dose dry powder inhaler, containing an inhalable pharmaceutical composition of the invention.

In a further embodiment, Compound (I), or a pharmaceutically acceptable salt thereof, administered by means of a metered dose inhaler (MDI), particularly a pressurised metered dose inhaler (pMDI). The pMDI contains the active as a suitable solution or suspension in a pressurised container. The active is delivered by actuating a valve on the pMDI device. Actuation may be manual or breath actuated. In manually actuated pMDIs the device is actuated by the user as they inhale, for example by pressing a suitable release mechanism on the pMDI device. Breath actuated pMDIs are actuated when the patient inhales through the mouthpiece of the pMDI. This can be advantageous as the actuation of the device is timed with the patients' inhalation and can result in a more consistent dosing of the active. An example of a pMDI device includes Rapihaler® (AstraZeneca).

An inhalable pharmaceutical composition for use in a pMDI can be prepared by dissolving or dispersing Compound (I), or a pharmaceutically acceptable salt thereof, in a suitable propellant and with or without additional excipients such as solvents (for example ethanol), surfactants, lubricants, preservatives or stabilising agents. Suitable propellants include hydrocarbon, chlorofluorocarbon and hydrofluroalkane (e.g. heptafluoroalkane) propellants, or mixtures of any such propellants. Suitable propellants are P134a and P227, each of which may be used alone or in combination with other propellants and/or surfactant and/or other excipients. When Compound (I), or a pharmaceutically acceptable salt thereof, is used as a suspension, the compound is suitably present in finely divided form (having a mass median diameter generally equal to or less than 10 µm, preferably equal to or less than 5 µm).

In a further embodiment, Compound (I), or a pharmaceutically acceptable salt thereof, is administered by means of a metered dose inhaler in combination with a spacer. Suitable spacers are well known and include Nebuchamber® (AstraZeneca) or Volumatic® (GSK).

In a further embodiment, Compound (I), or a pharmaceutically acceptable salt thereof, is administered by means of a nebuliser. Suitable nebulisers are well known.

An inhalable pharmaceutical composition for use in a nebuliser can be prepared by dispersing or preferably dissolving the Compound (I), or a pharmaceutically acceptable salt thereof, in a suitable aqueous medium. The composition may also include for example suitable pH and/or tonicity adjustment, surfactants and preservatives. In a further embodiment, Compound (I), or a pharmaceutically acceptable salt thereof, is administered nasally as a spray from a suitable nasal delivery device, for example a spray pump or an MDI adapted for nasal delivery. Alternatively, the salt could be administered nasally as a powder using a suitable DPI device e.g. Rhinocort® Turbuhaler® (AstraZeneca).

A nasally inhalable pharmaceutical composition for use in a spray pump or MDI nasal delivery device can be prepared by dispersing or dissolving the Compound (I), or a pharmaceutically acceptable salt thereof, in a suitable aqueous medium similar to those described above for inhalation via an MDI device. Suitable dry powder compositions for nasal delivery are as hereinbefore described in relation to DPI delivery. However, where it is desirable to limit the penetration of the compound into the lung and keep the compound in the nasal cavity, it may be necessary to use the compound as larger particle sizes, for example with an average particle diameter greater than about 10 µm, for example from 10 µm to 50 µm.

Accordingly, the present invention also provides an inhaler device suitable for nasal administration (for example a dry powder inhaler, in particular a multiple unit dose dry powder inhaler, or a pMDI inhaler) containing an inhalable pharmaceutical composition of the invention.

Pharmaceutical Compositions for External Topical Administration

When Compound (I), or a pharmaceutically acceptable salt thereof, is administered as an external topical pharmaceutical composition, suitable compositions include, for example, ointments, lotions, creams, gels, tapes, transdermal patches, cataplasms, or powders for external administration.

Ointments, creams and gels suitably contain Compound (I) in an amount of about 0.01-10 w/w %, and further comprise for example, one or more additional excipients including thickening agents, an aqueous or oily base, a gelling agent or a solvent. Suitable aqueous/oily bases include water and/or oil such as liquid paraffin, a vegetable oil such as arachis oil or castor oil. Examples of suitable solvents include polyethylene glycol. Examples of suitable thickening and gelling agents include soft paraffin, aluminium stearate, cetostearic alcohol, polyethylene glycol, sheep fat, beeswax, carboxypolymethylene and cellulose derivatives, glyceryl monostearate and/or nonionic emulsifiers.

Lotions suitably contain Compound (I) in an amount of about 0.01-10 w/w % and further comprise for example, one or more additional excipients including an aqueous or oily base, emulsifiers, stabilizers, dispersing agents, precipitation inhibitors or thickening agents.

Powders for external use suitably contain the Compound (I) in an amount of 0.01-10 w/w %, and it may be formulated using a suitable powdery base such as talc, lactose and starch.

The pharmaceutical compositions for external topical Administration may be particularly suitable for the treatment of skin conditions mentioned herein (for example, atopic dermatitis, actinic keratosis, pre-cancerous lesions or cutaneous vial infections).

Compound (I), or a pharmaceutically acceptable salt thereof, may also be administered in conjunction with other compounds used for the treatment of the above conditions.

The invention therefore further relates to combination therapies wherein Compound (I), or a pharmaceutically acceptable salt thereof, is administered concurrently or sequentially or as a combined preparation with another therapeutic agent or agents, for the treatment of one or more of the conditions listed above. For example Compound (I), or a pharmaceutically acceptable salt thereof, may be combined with one or more of the agents listed below:

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 23, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxifylline.

In addition the invention relates to a combination of a compound of the invention, with a monoclonal antibody targeting B-Lymphocytes (such as CD20 (rituximab), MRAaIL16R and T-Lymphocytes, CTLA4-Ig (abatacept), HuMax I1-15).

The present invention still further relates to the combination of a compound of the invention, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175;

Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY×1005.

The present invention further relates to the combination of a compound of the invention, and a receptor antagonist for leukotrienes (LT) B4, LTC4, LTD4, and LTE4. selected from the group consisting of the phenothiazin-3-1s such as L-651, 392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY× 7195.

The present invention still further relates to the combination of a compound of the invention, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, and a proton pump inhibitor (such as omeprazole) or a gastroprotective histamine type 2 receptor antagonist.

The present invention further relates to the combination of a compound of the invention, and an antagonist of the histamine type 4 receptor.

The present invention still further relates to the combination of a compound of the invention, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine, telenzepine or tolterodine.

The present invention still further relates to the combination of a compound of the invention, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof, indacaterol, milveterol or carmoterol.

The present invention further relates to the combination of a compound of the invention, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, with an agent that modulates a nuclear hormone receptor such as PPARs.

The present invention still further relates to the combination of a compound of the invention, together with an immunoglobulin (Ig) or Ig preparation or an antagonist or antibody modulating Ig function such as anti-IgE (for example omalizumab).

The present invention further relates to the combination of a compound of the invention, and another systemic or topically-applied anti-inflammatory agent, such as thalidomide or a derivative thereof, a retinoid, dithranol or calcipotriol.

The present invention still further relates to the combination of a compound of the invention, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxifylline; thrombolytic, or an anticoagulant such as a platelet aggregation inhibitor.

The present invention further relates to the combination of a compound of the invention, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, together with a parenterally or topically-applied (including inhaled) local anaesthetic agent such as lignocaine or a derivative thereof.

A compound of the present invention can also be used in combination with an anti-osteoporosis agent including a hormonal agent such as raloxifene, or a biphosphonate such as alendronate.

The present invention still further relates to the combination of a compound of the invention, together with a: (i) tryptase inhibitor; (ii) platelet activating factor (PAF) antagonist; (iii) interleukin converting enzyme (ICE) inhibitor; (iv)

IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example gefitinib or imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-$B_1$- or $B_2$-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $NK_1$. or $NK_3$. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS.

A compound of the invention, can also be used in combination with an existing therapeutic agent for the treatment of cancer, for example suitable agents include:
(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);
(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;
(iii) an agent which inhibits cancer cell invasion (for example a metalloproteinase inhibitor like marimastat or an inhibitor of urokinase plasminogen activator receptor function);
(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;
(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);
(vi) a vascular damaging agent such as combretastatin A4, or a compound disclosed in WO 99/02166, WO 00/40529, WO 00/41669, WO 01/92224, WO 02/04434 or WO 02/08213;
(vii) an agent used in antisense therapy, for example one directed to one of the targets listed above, such as ISIS 2503, an anti-ras antisense;
(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or
(ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a further aspect the present invention provides a combination product (for example for use as a medicament for the treatment of one of the conditions listed herein such as COPD, asthma or allergic rhinitis) comprising Compound (I), or a pharmaceutically acceptable salt thereof as hereinbefore defined, and one or more agents independently selected from:
 a) a PDE4 inhibitor including an inhibitor of the isoform PDE4D;
 b) a β-adrenoceptor agonist such as metaproterenol, isoproterenol, isoprenaline, albuterol, salbutamol, formoterol, salmeterol, terbutaline, orciprenaline, bitolterol mesylate, pirbuterol, indacaterol or carmoterol;
 c) a muscarinic receptor antagonist (for example a M1, M2 or M3 antagonist, such as a selective M3 antagonist) such as ipratropium bromide, tiotropium bromide, oxitropium bromide, pirenzepine, telenzepine or tolterodine;
 d) a modulator of chemokine receptor function (such as a CCR1 or CCR8 receptor antagonist);
 e) an inhibitor of kinase function;
 f) a non-steroidal glucocorticoid receptor agonist;
 g) a steroidal glucocorticoid receptor agonist;
 h) a protease inhibitor (such as a MMP12 or MMP9 inhibitor); and
 i) an antiproliferative agent.

In another aspect, the invention provides a kit comprising a preparation of a first active ingredient which is Compound (I)

or a pharmaceutically acceptable salt thereof as hereinbefore defined, and a preparation of one or more second active ingredient(s) selected from:
a) a PDE4 inhibitor including an inhibitor of the isoform PDE4D;
b) a β-adrenoceptor agonist such as metaproterenol, isoproterenol, isoprenaline, albuterol, salbutamol, formoterol, salmeterol, terbutaline, orciprenaline, bitolterol mesylate, pirbuterol, indacaterol or carmoterol;
c) a muscarinic receptor antagonist (for example a M1, M2 or M3 antagonist, such as a selective M3 antagonist) such as ipratropium bromide, tiotropium bromide, oxitropium bromide, pirenzepine, telenzepine or tolterodine;
d) a modulator of chemokine receptor function (such as a CCR1 or CCR8 receptor antagonist);
e) an inhibitor of kinase function;
f) a non-steroidal glucocorticoid receptor agonist;
g) a steroidal glucocorticoid receptor agonist;
h) a protease inhibitor (such as a MMP12 or MMP9 inhibitor); and
i) an antiproliferative agent;
and instructions for the simultaneous, sequential or separate administration of the preparations to a patient in need thereof.

EXAMPLES

Figure 1:
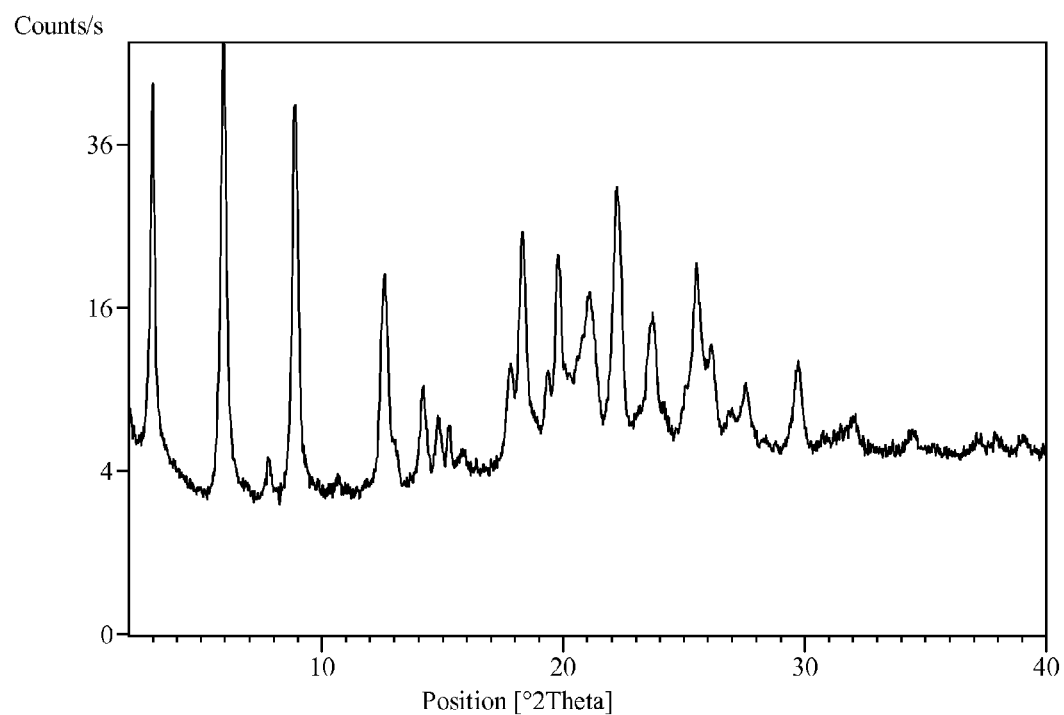
FIG. 1 is an X-ray powder diffraction pattern of Compound (I) Form A measured at a wavelength of 1.5418 Å. The x-axis shows the 2-theta value and the y-axis the counts.

The present invention will now be further illustrated by reference to the following examples in which, unless stated otherwise:
(i) Temperatures are given in degrees Celsius (° C.); operations were carried out at room or ambient temperature, that is, at a temperature in the range of 18-25° C.
(ii) In general, the course of reactions was followed by HPLC and reaction times are given for illustration only.
(iii) Yields are given for illustration only and are not necessarily those which can be obtained by diligent process development; preparations were repeated if more material was required.
(iv) Chemical symbols have their usual meanings; SI units and symbols are used.
(v) Solvent ratios are given in volume:volume (v/v) terms.
(vi) Unless stated otherwise, starting materials were commercially available.
(vii) Unless stated otherwise, example names have been generated using the IUPAC naming function of ACD Labs Version 10 (Advanced Chemistry Development, Inc.).

General Methods $^1$H NMR spectra were recorded at 298K on a Varian Unity Inova 300 spectrometer operating at 300 MHz; or a Bruker AVANCE 400 FT NMR spectrometer, operating at 400 MHz.

RPHPLC means reversed phase preparative HPLC using Waters Symmetry C8, Xterra, XBridge or Phenomenex Gemini columns using acetonitrile and either aqueous ammonium acetate, ammonia, formic acid or trifluoroacetic acid as buffer where appropriate. Column chromatography was carried out on silica gel. Treating with SCX means the mixture was absorbed on SCX and eluted with an appropriate solvent such as methanol or acetonitrile then the free base product eluted with aqueous ammonia/methanol.

XRPD samples were mounted on single silicon crystal (SSC) wafer mounts and powder X-ray diffraction was recorded with a Theta-Theta Philips CubiX PRO wavelength of X-rays 1.5418 Å (Cu source, Voltage 45 kV, filament emission 40 mA). Samples were scanned from 2-40° 2Theta using a 0.02° step width and a 100 second count time using an X'celerator detector (active length 2.13° 2Theta). Relative intensities of the peaks observed are given according to the following categories: very strong (vs) 25-100%, strong (s) 10-25%, medium (m) 3-10% and weak (w) 1-3%.

Differential scanning calorimetry was performed using a TA Instruments model Q1000. A sample (approximately 0.5-2 mg) was weighed into an aluminium sample pan and transferred to the DSC. The instrument was purged with nitrogen at 50 mL/min and data collected between 25° C. and 300° C., using a linear heating rate of 10° C./minute. Mass spectra were run on an Agilent 100 HPLCMS equipped with a multimode source.

ABBREVIATIONS

The following abbreviations have been used.

aq. aqueous
DCM: dichloromethane
DMF: N,N-dimethylformamide
DMSO: dimethylsulfoxide
EtOAc: ethyl acetate
hrs: hours
MeCN: acetonitrile
MeOH: methanol
MP: melting point
MS: mass spectrometry
MTBE: tert-butyl methyl ether
NMP: N-methyl 2-pyrrolidone
mins: minutes
rt: room temperature
THF: tetrahydrofuran

Example 1

Methyl [4-({[3-(6-amino-2-butoxy-8-oxo-7,8-dihydro-9H-purin-9-yl)propyl][3-(piperidin-1-yl)propyl]amino}methyl)phenyl]acetate

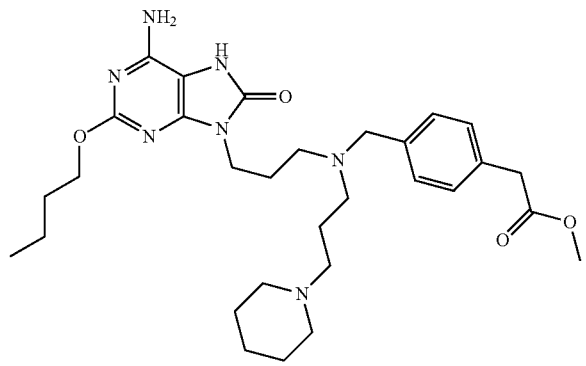 [SMILES: CCCCOc1nc(N)c2[nH]c(=O)n(CCCN(CCCN3CCCCC3)Cc3ccc(CC(=O)OC)cc3)c2n1]

To the product from step (iv) of Example 1 (0.16 g) in DCM (10 mL) and piperidine (1 mL) was added and the mixture stirred at rt for 48 hrs. The mixture was concentrated in vacuo and purified via RPHPLC to give the title compound as a white solid (21 mg); MS multimode (+) 568; $^1$H NMR CDCl$_3$: δ 7.15 (q, 4H), 5.50 (s, 2H), 4.26 (t, 2H), 3.85 (t, 2H), 3.74 (s, 3H), 3.63 (s, 2H), 3.47 (s, 2H), 2.80-1.40 (m, 24H), 0.97 (t, 3H)

The compound prepared in Example 1 was crystalline (Form A) and provided the XRPD pattern shown in FIG. 1 when measured at a wavelength of 1.5418 Å. The most prominent peaks of the XRPD pattern for Form A are shown in Table 1 in the description.

Figure 2:
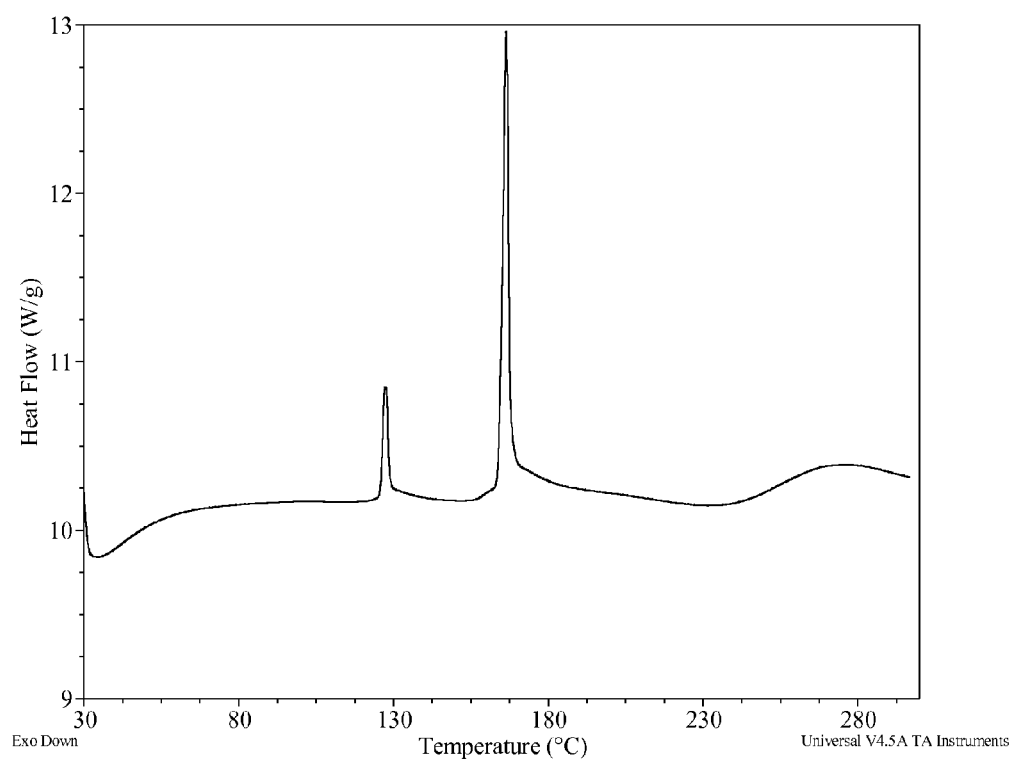
FIG. 2 is a differential scanning calorimetry (DSC) trace for Compound (I) Form A. The x-axis shows temperature (° C.) and the y-axis heat flow (watts/g).

When heated in a Differential Scanning calorimeter (DSC) (conditions as described in the Examples section) Form A exhibits a melting endotherm with an onset temperature of about 125° C. and a second melting endotherm with an onset temperature of 164° C., as illustrated in FIG. 2.

The methyl {4-[([3-(6-amino-2-butoxy-8-oxo-7,8-dihydro-9H-purin-9-yl)propyl]{3-[(methylsulfonyl)oxy]propyl}amino)methyl]phenyl}acetate starting material was prepared as follows.

(i) (4-Formylphenyl)acetic acid

[4-(Bromomethyl)phenyl]acetic acid (4.6 g) and cupric nitrate trihydrate (5 g) were suspended in water (50 mL) and heated at reflux for 1 hr. The solution was allowed to cool and the resulting white solid collected and washed with water to give the subtitle compound (2.06 g); MS multimode (+) 165

(ii) [4-({[3-(6-Amino-2-butoxy-8-oxo-7,8-dihydro-9H-purin-9-yl)propyl](3-hydroxypropyl)amino}methyl)phenyl]acetic acid

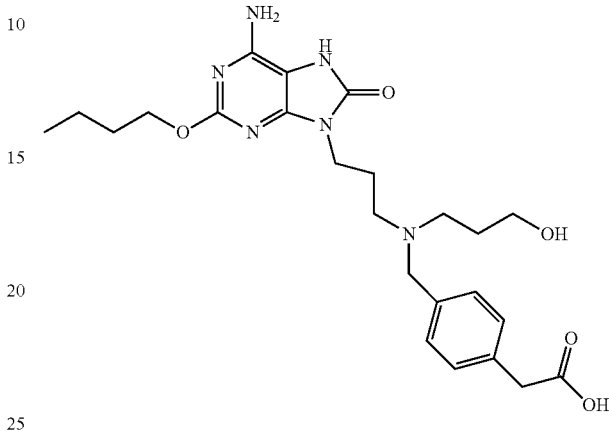

To 6-amino-2-butoxy-9-{3-[(3-hydroxypropyl)amino]propyl}-7,9-dihydro-8H-purin-8-one (described in WO2007/031726 Example 1 step (viii)) (0.5 g) in NMP, the product from step (i) (0.35 g) was added and the mixture stirred for 10 mins. Sodium triacetoxyborohydride (1.25 g) was then added and stirred at rt for 16 hrs. The reaction mixture was diluted with water and passed through a SCX column, eluted with MeCN/2% NH$_3$ (aq), and solvent removed to give the crude product. The product was purified via RPHPLC to afford the subtitle compound as a solid; $^1$H NMR DMSO 67.14-7.20 (m, 4H), 6.40 (s, 2H), 4.12 (t, 2H), 3.67 (t, 2H), 3.51 (s, 2H), 3.47 (s, 2H), 3.39 (t, 2H), 2.36-2.44 (m, 4H), 1.78-1.86 (m, 2H), 1.52-1.65 (m, 4H), 1.32-1.41 (m, 2H), 0.90 (t, 3H) MS multimode (+) 487

(iii) Methyl [4-({[3-(6-amino-2-butoxy-8-oxo-7,8-dihydro-9H-purin-9-yl)propyl](3-hydroxypropyl)amino}methyl)phenyl]acetate To the product from step (ii) (0.38 g) in MeOH, chlorotrimethylsilane (3 mL) was added and the mixture stirred at rt for 1 hr. The solvent was removed to give the subtitle compound as a cream solid (0.39 g); MS multimode (+) 501.

(iv) Methyl {4-[([3-(6-amino-2-butoxy-8-oxo-7,8-dihydro-9H-purin-9-yl)propyl][3-[(methylsulfonyl)oxy]propyl}amino)methyl]phenyl}acetate The product from step (iii) (0.39 g) was dissolved in DCM (20 mL) and triethylamine (0.15 g) added, followed by addition of methanesulfonyl chloride (0.3 mL) and the mixture stirred for 5 hrs. The mixture was concentrated in vacuo to afford the subtitle compound as a crude product (0.45 g); MS multimode (+) 579.

Example 2

Methyl [4-{[[3-(6-amino-2-butoxy-8-oxo-7,8-dihydro-9H-purin-9-yl)propyl](3-piperidin-1-ylpropyl)amino]methyl}phenyl]acetate hydrochloride

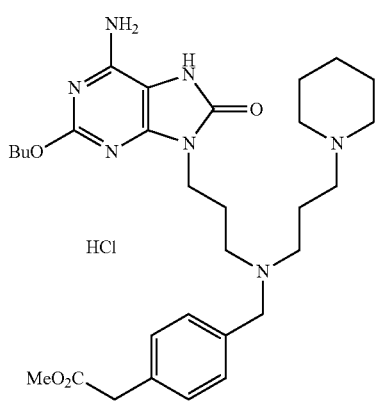

A mixture of methyl [4-{[[3-(6-amino-2-butoxy-8-oxo-7,8-dihydro-9H-purin-9-yl)propyl](3-piperidin-1-ylpropyl)amino]methyl}phenyl]acetate (6.0 g, 10.8 mmol) in MeOH (30 g) was stirred at 8° C. for 10 min. To the suspension, 35% aqueous HCl (1.1 g, 10.67 mmol) in MeOH (6 g mL) was added dropwise and warmed to 23° C. To the mixture was added more MeOH (3 g). MTBE (78 g) was added to the mixture, which was then stirred at 20° C. for 30 min. After seeding and stirring for 30 min, MTBE (42 g) was added, the suspension cooled to 3° C. and stirred for 1 hr. Then the suspension was filtered and collected solid washed with MTBE (15 g) and dried to give the title compound. M.P. 137-139° C. Yield 5.7 g, 90%; $^1$H NMR (DMSO-d$_6$) δ 10.08 (br, 1H), 7.24 (d, 2H), 7.17 (d, 2H), 6.53 (br, 2H), 4.11 (t, 2H), 3.68 (t, 4H), 3.65 (s, 3H), 3.50 (s, 2H), 3.07-2.95 (m, 6H), 2.39 (m, 4H), 1.84-1.51 (m, 12H), 1.38-1.33 (m, 2H), 0.89 (t, 3H).

Figure 3:
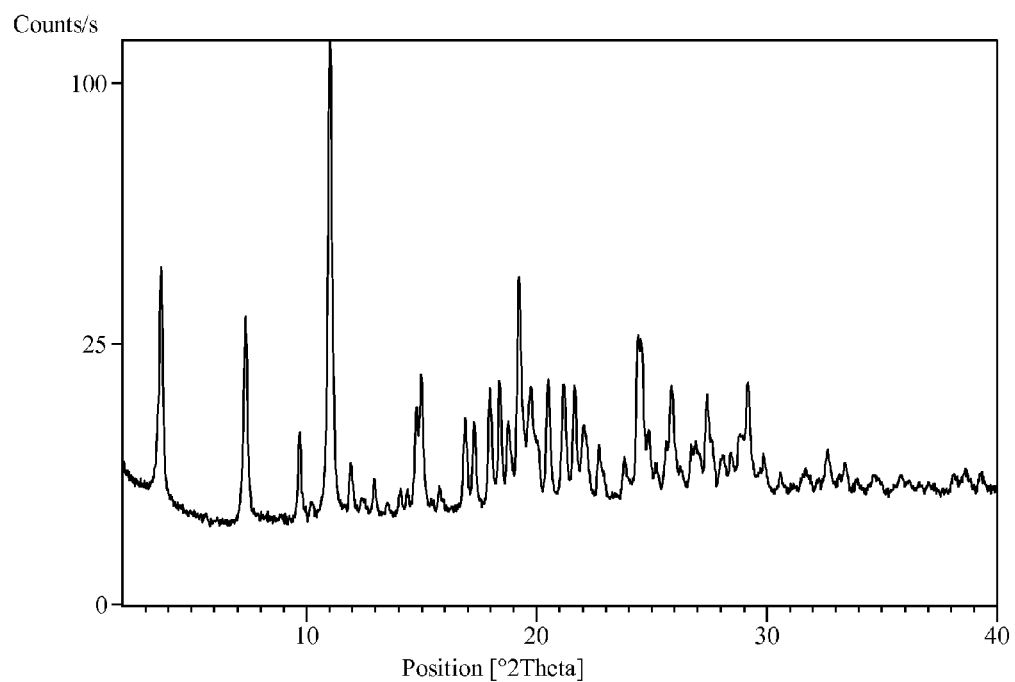
FIG. 3 is an X-ray powder diffraction pattern of Compound (I) Form B measured at a wavelength of 1.5418 Å. The x-axis shows the 2-theta value and the y-axis the counts.

The compound prepared in Example 2 was crystalline (Form B) and provided the XRPD pattern shown in FIG. 3 when measured at a wavelength of 1.5418 Å. The most prominent peaks of the XRPD pattern for Form B are shown in Table 2 in the description.

Figure 4:
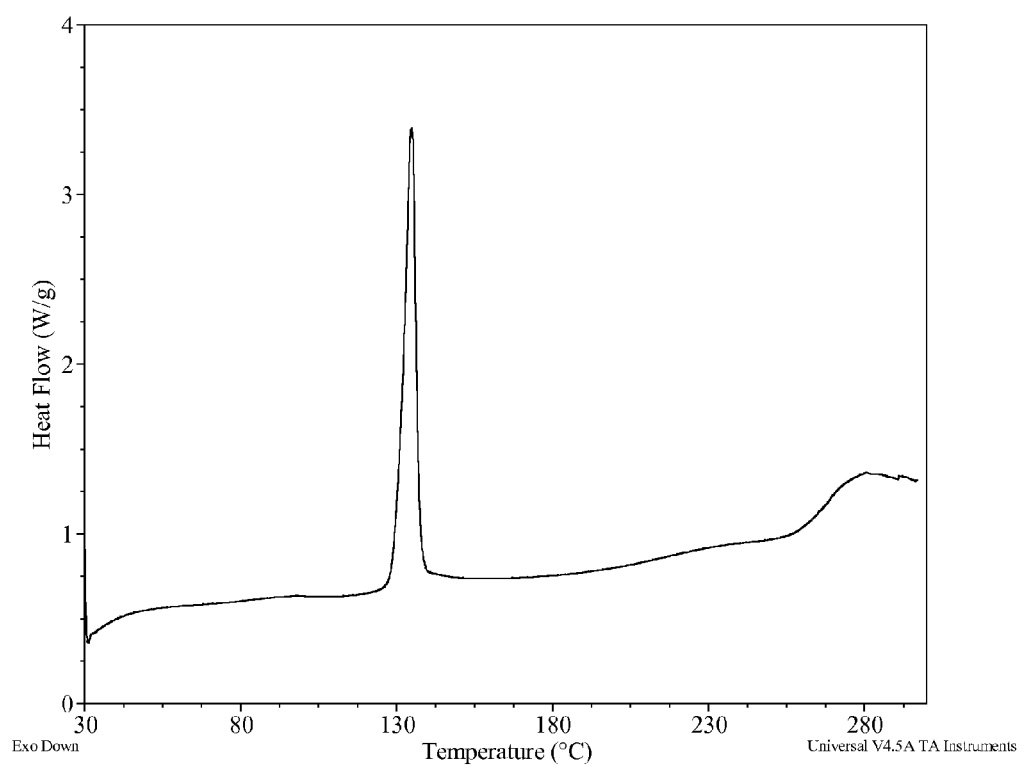
FIG. 4 is a differential scanning calorimetry (DSC) trace for Compound (I) Form B. The x-axis shows temperature (° C.) and the y-axis heat flow (watts/g).

When heated in a Differential Scanning calorimeter (DSC) (conditions as described in the Examples section) Form B exhibits a melting endotherm with an onset temperature at about 131° C., as illustrated in FIG. 4.

The methyl [4-{[[3-(6-amino-2-butoxy-8-oxo-7,8-dihydro-9H-purin-9-yl)propyl](3-piperidin-1-ylpropyl)amino]methyl}phenyl]acetate starting material was prepared as follows:

(i) Methyl [4-(bromomethyl)phenyl]acetate

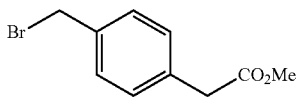 [SMILES: COC(=O)Cc1ccc(CBr)cc1]

To a mixture of p-bromomethylphenylacetic acid (50.0 g, 218 mmol) in MeOH (125 g) and toluene (250 g), was added thionyl chloride (15.6 g) dropwise at 0° C. and stirred for 3 hr. Separately NaHCO$_3$ (33 g, 393 mmol) was dissolved in water (540 g), mixed with toluene (200 g) and cooled to 0° C. The reaction solution described above was added dropwise to the mixture and stirred for 1 hr. The aqueous layer was removed and the organic layer washed with water. The solution was then concentrated under reduced pressure at a temperature below 40° C. to give the subtitle compound as a crude product (58.9 g) used directly in the following reaction. $^1$H NMR (DMSO-d$_6$) δ 7.37 (d, 2H), 7.34 (d, 2H), 4.62 (s, 2H), 3.73 (s, 2H), 3.63 (s, 3H)

(ii) Methyl (4-formylphenyl)acetate

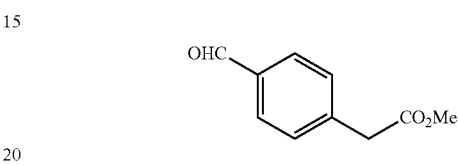

To a mixture of N-methylmorpholine-N-oxide (63.9 g, 545 mmol) in MeCN (848 g) and toluene (742 g), was added a solution of methyl [4-(bromomethyl)phenyl]acetate (53.0 g) in toluene (212 g) at 0 to 25° C. After stirring for 5 hr, water (106 g) was added to the reaction mixture. The aqueous layer was removed and remaining MeCN in the organic layer was removed under reduced pressure. The remaining toluene solution was washed with water twice (530 g×2), and concentrated under reduced pressure at a temperature below 40° C. until the weight of the solution was 233 g. An activated charcoal (3 g) was added to the solution and removed by filtration. To the solution was added 2,6-dibutyl-4-hydroxytoluene (152 mg), and concentrated under reduced pressure to give the subtitle compound. Yield 30.9 g, 79% from methyl [4-(bromomethyl)phenyl]acetate; $^1$H NMR (DMSO-d$_6$) δ 9.99 (s, 1H), 7.87 (d, 2H), 7.86 (d, 2H), 3.83 (s, 2H), 3.63 (s, 3H)

(iii) 3-(6-Amino-2-butoxy-8-methoxy-9H-purin-9-yl)propan-1-ol

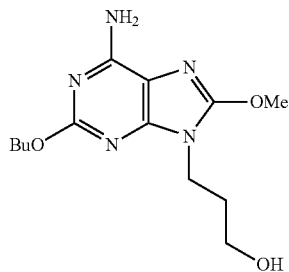

To a suspension of 2-butoxy-8-methoxy-9H-purin-6-amine trifluoroacetate (described in EP 1 728 793, Example 2-1, step (vi)) (20.0 g, 56.9 mmol) in NMP (111 g) was added water (1.7 g) and K$_2$CO$_3$ (23.61 g, 170.8 mmol). To the mixture 1-acetoxy-3-bromopropane (12.4 g, 68.3 mmol) was added and the mixture stirred at 30° C. for 3 hr. To the solution was added MeOH (79 g) and 2% aqueous NaOH (100 g) and stirred at 70° C. for 3 hr. After adding water (200 g) and cooling to 7° C., the suspension was filtered and the collected solid dried to give the subtitle compound as white solid. Yield 13.0 g, 78%; $^1$H NMR (DMSO-d$_6$) δ 6.77 (bs, 2H), 4.57 (t, 1H), 4.16 (t, 2H), 4.04 (s, 3H), 3.89 (t, 2H), 3.42-3.38 (m, 2H), 1.85-1.78 (m, 2H), 1.68-1.61 (m, 2H), 1.41-1.35 (m, 2H), 0.92 (t, 3H)

(iv) 3-(6-Amino-2-butoxy-8-methoxy-9H-purin-9-yl)propyl methanesulfonate

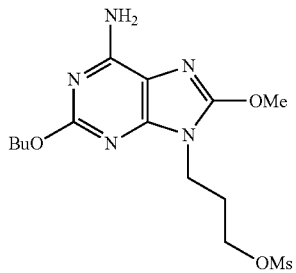

To a solution of 3-(6-amino-2-butoxy-8-methoxy-9H-purin-9-yl)propan-1-ol (18.0 g, 61.0 mmol) in NMP (146 g) was added triethylamine (9.3 g, 91.4 mmol) and the mixture stirred at 5° C. Methanesulfonylchloride (9.1 g, 79.2 mmol) was added dropwise to the solution and stirred at 5° C. for 30 min. Water (144 g) was added, the mixture stirred for 1 hr and the suspension filtered to give the subtitle compound as water wet cake, which was directly used in the next reaction. Yield 42.4 g as a crude product.

(v) 6-Amino-2-butoxy-9-{3-[(3-piperidin-1-ylpropyl)amino]propyl}-7,9-dihydro-8H-purin-8-one dimaleate

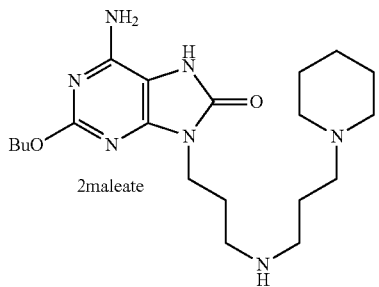

To 3-(piperidin-1-yl)propan-1-amine (86.7 g, 609 mmol) was added 3-(6-amino-2-butoxy-8-methoxy-9H-purin-9-yl)propyl methanesulfonate (wet cake as described in step (iv) above) separately at 0 to 10° C. and stirred for 16 hr at room temperature. The solution was cooled to 3° C. and 15% aqueous NaCl (244 g) added. To the mixture was added toluene (170 mL) and THF (170 mL) and the aqueous layer separated. The aqueous layer was extracted with toluene (85 mL) and THF (85 mL) four times, and combined organic layer was washed with 20% aqueous NaCl (389 g).

35% HCl (63.5 g, 609 mmol) was added dropwise to the solution at a temperature between 2 to 20° C. and the mixture stirred at 22° C. for 7 hr. To the mixture 35% HCl (31.8 g, 305 mmol) was added and the mixture stirred for 3 hr. The reaction mixture was concentrated under reduced pressure at 40° C. until a weight of the mixture was 136 g.

20% aqueous NaOH (72 g), 10% aqueous $Na_2CO_3$ (280 g) and $CHCl_3$ (702 g) were added to the mixture (31 g). The mixture was warmed to 53° C. and the aqueous layer removed. The organic layer was concentrated under reduced pressure at 30 to 40° C. MeOH (124 g) was poured into the mixture and the solution concentrated until the weight of the mixture was 52 g. MeOH (50 g) was then poured again and the mixture warmed to 50° C.

A solution of maleic acid (14.2 g, 121.9 mmol) in MeOH (50 g) was added dropwise to the solution at 50° C., followed by MeOH (124 g). The mixture was stirred at 50° C. for 1 hr and cooled to 5° C. After stirring for 30 min, the suspension was filtered and collected solid was washed with MeOH and dried to give the title compound as a white solid. Yield 31.6 g, 81% from 3-(6-amino-2-butoxy-8-methoxy-9H-purin-9-yl)propan-1-ol; $^1$H NMR (DMSO-$d_6$) δ 9.96 (s, 1H), 8.36 (bs, 1H), 6.49 (s, 2H), 6.01 (s, 4H), 4.14 (t, 2H), 3.76 (t, 2H), 2.96-2.66 (br+t, 9H), 2.00-1.34 (m, 15H), 0.91 (t, 3H)

(vi) Methyl (4-{[[3-(6-amino-2-butoxy-8-oxo-7,8-dihydro-9H-purin-9-yl)propyl](3-piperidin-1-ylpropyl)amino]methyl}phenyl)acetate

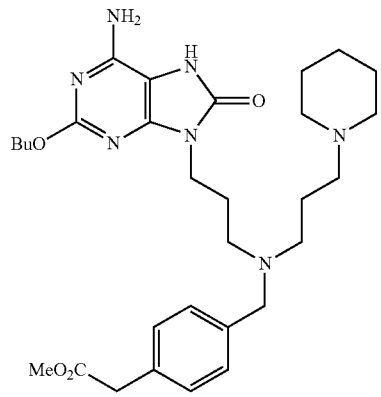

A mixture of 6-amino-2-butoxy-9-{3-[(3-piperidin-1-ylpropyl)amino]propyl}-7,9-dihydro-8H-purin-8-one dimaleate (20.0 g, 31.3 mmol), triethylamine (9.5 g, 94.1 mmol) and NMP (72 g) was stirred at 25° C. for 30 min. Sodium triacetoxyborohydride (11.3 g, 53.3 mmol) was added to the solution and stirred for 15 min. A solution of methyl (4-formylphenyl)acetate (8.4 g, 47.1 mmol) in NMP (10.3 g) was added to the solution and the mixture stirred for 8 hr. Then NMP (41 g) was poured into the reaction solution and cooled to 5° C. To the solution was added cold water (200 g) dropwise and the mixture stirred. The reaction mixture was adjusted to pH9 by using 10% aqueous $Na_2CO_3$ and water (86 g) added. After stirring for 1 hr, the reaction mixture was filtered, the collecting solid washed with cooled water and dried to give the crude subtitle compound as a white solid. Yield 15.0 g, 84%.

A mixture of the crude subtitle compound (7.0 g, 12.3 mmol), lithium bromide (1.1 g, 12.3 mmol), and acetone (66 g) was stirred at 50° C. for 2 hr. The mixture was cooled to 18° C. and water (21 g) was added and the mixture stirred for 10 min. After seeding, the mixture was stirred for 15 min. Water (105 g) was added and the mixture stirred for 30 min and cooled to 10° C. After stirring for 30 min, the reaction mixture was filtered, the collecting solid washed with cooled water (35 g) and dried to give the subtitle product as a white solid; $^1$H NMR (DMSO-$d_6$) δ 10.06 (brs, 1H), 7.23 (d, 2H), 7.15 (d, 2H), 6.46 (br, 2H), 4.11 (t, 2H), 3.67 (t, 2H), 3.63 (s, 2H), 3.60 (s, 3H), 3.46 (s, 2H), 2.38 (t, 2H), 2.33 (t, 2H), 2.18-2.12 (m, 6H), 1.81 (m, 2H), 1.61 (m, 2H), 1.51-1.42 (m, 2H), 1.42-1.32 (m, 8H), 0.89 (t, 3H).

Example 3

Methyl [4-{[[3-(6-amino-2-butoxy-8-oxo-7,8-dihydro-9H-purin-9-yl)propyl](3-piperidin-1-ylpropyl) amino]methyl}phenyl]acetate hydrobromide

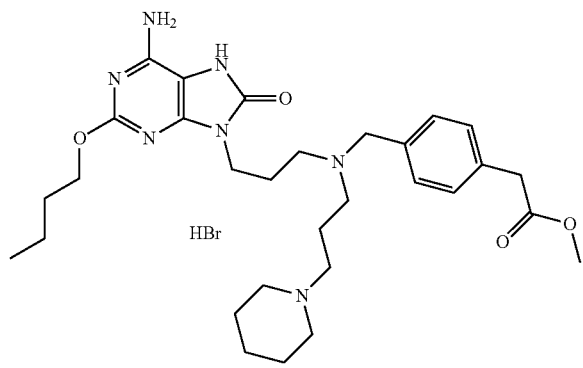 [SMILES: CCCCOc1nc(N)c2[nH]c(=O)n(CCCN(CCCN3CCCCC3)Cc3ccc(CC(=O)OC)cc3)c2n1 ; Br]

The product of Example 1 (0.81 g, 1.42 mmol) in MeOH (30 g) was dissolved in MeOH (8 mL) and 48% aqueous HBr solution (0.16 mL, 1.4 mmol) added. The mixture was stirred at rt for 1 hr and concentrated in vacuo. MeOH (1.6 mL) and MTBE (6.4 mL) was added to residue and the suspension stirred at rt for 4 days. The suspension was filtered, the collected solid washed with MTBE (50 mL) and dried to give the title compound (734 mg); MS multimode (+) 568; $^1$H NMR (DMSO-d$_6$): δ 9.86 (brs, 1H), 7.24 (d, 2H), 7.18 (d, 2H), 6.42 (br, 2H), 4.12 (t, 2H), 3.69 (t, 4H), 3.65 (s, 3H), 3.50 (s, 2H), 3.08-2.97 (m, 6H), 2.41 (m, 4H), 1.83-1.51 (m, 12H), 1.40-1.32 (m, 2H), 0.90 (t, 3H).

Figure 5:
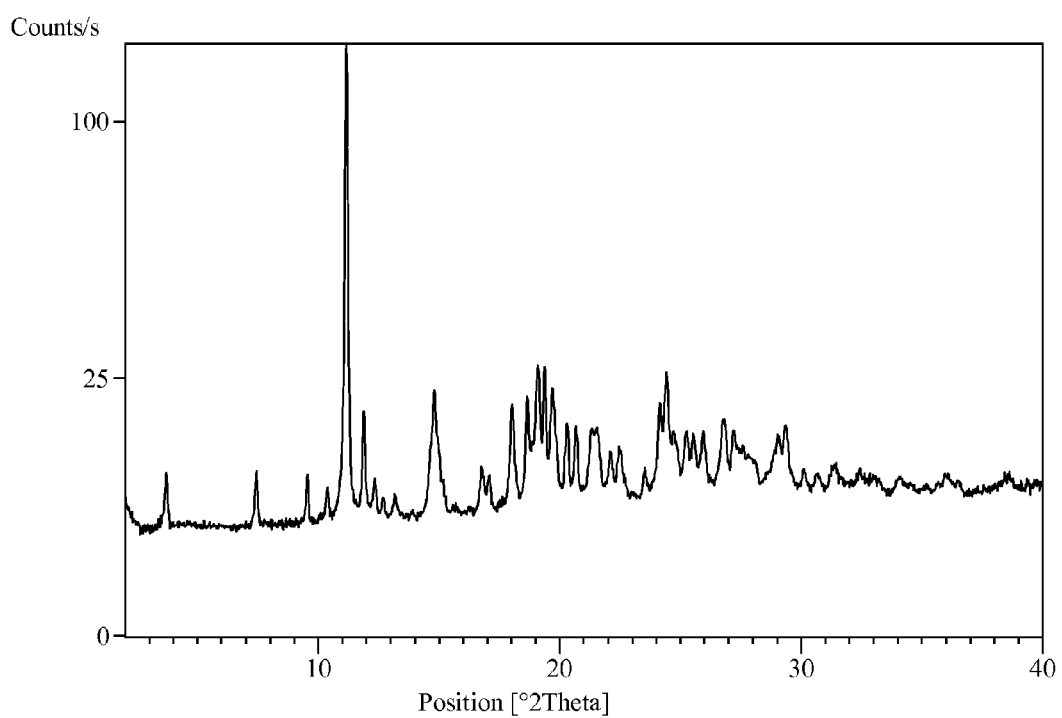
FIG. 5 is an X-ray powder diffraction pattern of Compound (I) Form C measured at a wavelength of 1.5418 Å. The x-axis shows the 2-theta value and the y-axis the counts.

The compound prepared in Example 3 was crystalline (Form C) and provided the XRPD pattern shown in FIG. 5 when measured at a wavelength of 1.5418 Å. The most prominent peaks of the XRPD pattern for Form C are shown in Table 3 in the description.

Figure 6:
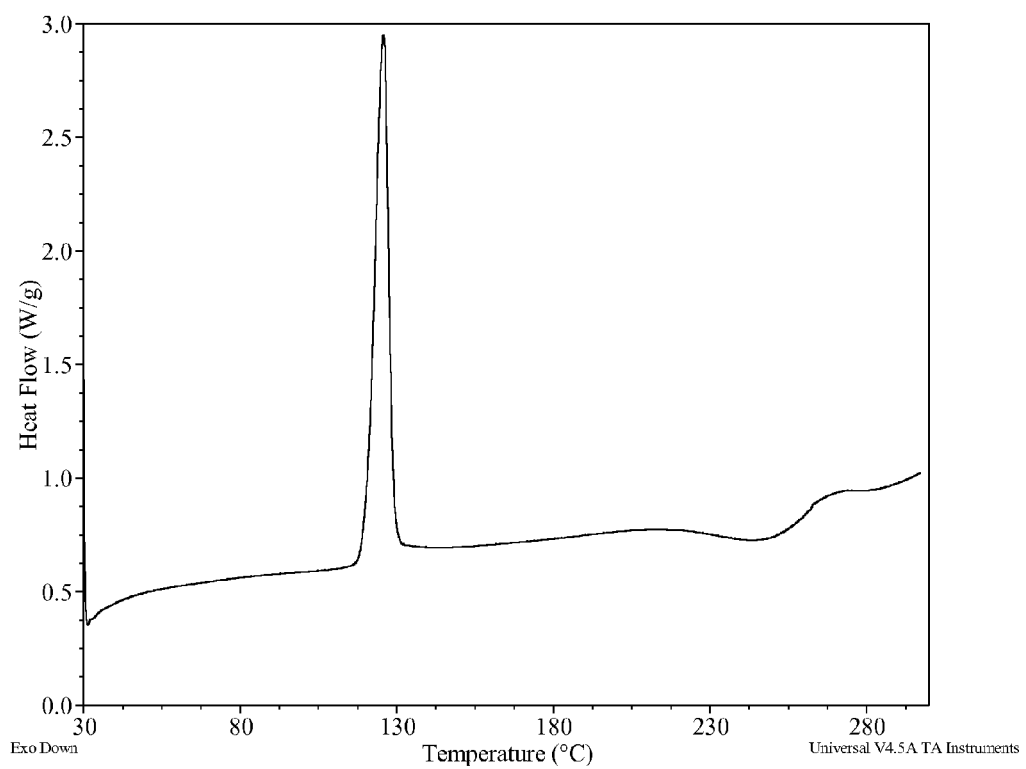
FIG. 6 is a differential scanning calorimetry (DSC) trace for Compound (I) Form C. The x-axis shows temperature (° C.) and the y-axis heat flow (watts/g).

When heated in a Differential Scanning calorimeter (DSC) (conditions as described in the Examples section) Form C exhibits a melting endotherm with an onset temperature at about 121° C., as illustrated in FIG. 6.

Comparative Example 1

Methyl [3-({[3-(6-amino-2-butoxy-8-oxo-7,8-dihydro-9H-purin-9-yl)propyl][3-(piperidin-1-yl)propyl] amino}methyl)phenyl]acetate

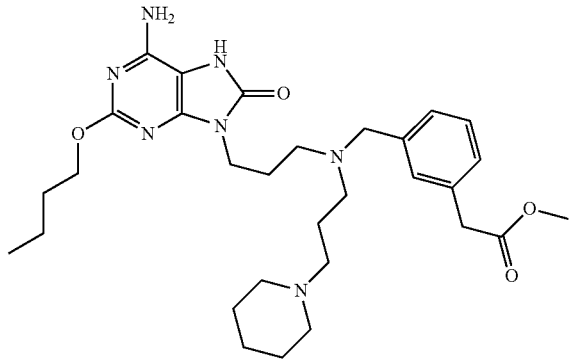 [SMILES: CCCCOc1nc(N)c2[nH]c(=O)n(CCCN(CCCN3CCCCC3)Cc3cccc(CC(=O)OC)c3)c2n1]

Methyl [3-({[3-(6-amino-2-butoxy-8-oxo-7,8-dihydro-9H-purin-9-yl)propyl](3-chloropropyl)amino}methyl)phenyl]acetate] (0.55 g) was added to a solution of piperidine (0.53 mL) in DMF (5 mL) and sodium iodide (0.32 g) and the mixture stirred at 25° C. overnight. Acetic acid (0.5 mL), MeOH (0.5 mL) and DMSO (0.1 mL) were then added and the suspension filtered. The product was purified via RPHPLC. The fractions containing the desired compound were evaporated to dryness and the product stirred in EtOAc-diethyl ether (1 mL-2 mL), the title compound was then collected as a white solid. (0.17 g); $^1$H NMR (DMSO) δ 9.79 (s, 1H), 7.28-7.04 (m, 4H), 6.36 (s, 2H), 4.12 (t, 2H), 3.72-3.61 (m, 4H), 3.59 (s, 3H), 3.48 (s, 2H), 2.45-2.30 (m, 5H), 2.25-2.09 (m, 6H), 1.90-1.73 (m, 2H), 1.67-1.56 (m, 2H), 1.55-1.25 (m, 8H), 0.90 (t, 3H); MS multimode (+) 568. The methyl [3-({[3-(6-amino-2-butoxy-8-oxo-7,8-dihydro-9H-purin-9-yl)propyl](3-chloropropyl)amino}methyl)phenyl]acetate] used as the starting material was prepared as follows:

(i) Methyl [3-({[3-(6-amino-2-butoxy-8-oxo-7,8-dihydro-9H-purin-9-yl)propyl](3-chloropropyl)amino}methyl)phenyl]acetate

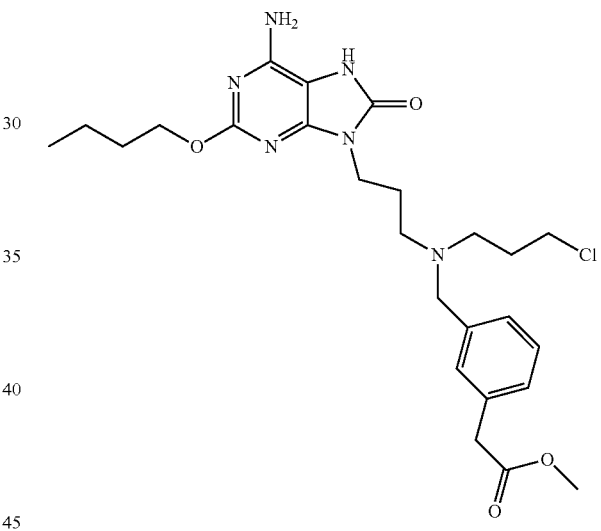

Methyl (3-{[[3-(6-amino-2-butoxy-8-oxo-7,8-dihydro-9H-purin-9-yl)propyl](3-hydroxypropyl)amino] methyl}phenyl)acetate (described in WO2007/1031726, Example 1 step (ix)) (534 mg) was suspended in DCM (5 mL) and thionyl chloride (0.09 mL) added. The reaction mixture was stirred at 25° C. overnight. The reaction was concentrated in vacuo to give the subtitle product (0.55 g); MS multimode (+) 520

Biological Activity

Compound (I) and pharmaceutically acceptable salts thereof have antedrug properties. An antedrug is defined as an active synthetic derivative that is designed to undergo biotransformations to a readily excretable less active form upon entry into the systemic circulation, therefore minimizing systemic side-effects. Thus, on administration, a compound of the invention is rapidly degraded enzymatically to yield a, degradation product having a substantially reduced medical effect. A medical effect as defined herein means a pharmacological activity of the compound of the invention, including specifically interferon inducing activity and/or suppression of IL4/IL5 production activity. The medical effect of the degradation product is preferably 10 times, more preferably 100 times less than that of the compound of the invention (i.e. parent compound). The pharmacological activity can be measured using methods known in the art, suitably using in vitro evaluation methods such as commercially available ELISA kits or the human TLR7 assay described below.

Human TLR7 Assay

Recombinant human TLR7 was stably expressed in a HEK293 cell line already stably expressing the pNiFty2-SEAP reporter plasmid; integration of the reporter gene was maintained by selection with the antibiotic zeocin. The most common variant sequence of human TLR7 (represented by the EMBL sequence AF240467) was cloned into the mammalian cell expression vector pUNO and transfected into this reporter cell-line. Transfectants with stable expression were selected using the antibiotic blasticidin. In this reporter cell-line, expression of secreted alkaline phosphatase (SEAP) is controlled by an NFkB/ELAM-1 composite promoter comprising five NFkB sites combined with the proximal ELAM-1 promoter. TLR signaling leads to the translocation of NFkB and activation of the promoter results in expression of the SEAP gene. TLR7-specific activation was assessed by determining the level of SEAP produced following overnight incubation of the cells at 37° C. with the standard compound in the presence of 0.1% (v/v) dimethylsulfoxide (DMSO). Concentration dependent induction of SEAP production by compounds was expressed as the concentration of compound which produced half of the maximal level of SEAP induction for that compound (pEC50).

Example 1 (Compound (I)) gave a mean pEC50 of 6.6 (n=6). Comparative Example 1 gave a mean pEC50 of 6.8 (n=2).

Human Skin Cytokine Production

Normal human skin biopsies were obtained, with informed consent, from healthy patients undergoing surgical cosmetic procedures. 3 mm full thickness skin biopsies were taken using a biopsy punch. A hole was cut in a Transwell filter (pore size 0.4 μm) using a punch and the skin biopsy inserted in the hole. The filter containing the biopsy was placed in the well of a 24-well culture plate containing 1.25 ml of culture medium (RPMI containing 1% heat-inactivated human serum) with the epidermis facing upwards at the liquid-air interface. Culture plates containing the biopsies were incubated at 37° C., in an atmosphere of 5% $CO_2$ in air, for 24 hours. Biopsies were cultured in the absence or presence of phytohaemagglutinin (PHA) (1 mg/ml) added to the culture medium to induce a cytokine response in the tissue. The test compound was applied topically (50 to the surface of the skin biopsies using a pipette followed by gentle rubbing on the skin surface. The concentration of the test compound applied was either the maximal solubility in phosphate citrate buffer pH 3.0 (4.1-4.4% w/w for Example I (Compound I)) or a ten-fold dilution from the maximal solubility. Supernatants were sampled 24 hours after the initiation of the cultures and were analysed for the production of the cytokine interleukin-13 (IL-13) by ELISA.

| Treatment | IL-13 (pg/ml) Mean ± SEM | % Inhibition of response |
|---|---|---|
| Control, vehicle | 0.8 ± 0.2 | |
| PHA, vehicle | 9.5 ± 2.1 | 0% |
| PHA, Compound I (max. solubility) | 1.9 ± 0.8 | 87% |
| PHA, Compound I (1/10 max. solubility) | 4.8 ± 0.8 | 55% |

CYP Inhibition

Substantial changes to overall exposure to a drug can arise from metabolic drug-drug interactions, and this may result in both an increased or decreased concentration of the drug in the blood and tissue, and in the formation of toxic and/or active metabolites. Hepatic metabolism occurs primarily via the cytochrome P450 family (CYP) of enzymes. Compounds with a reduced potency at the CYP family may exhibit an improved safety and efficacy profile (FDA Guidance for Industry—Drug Interaction Studies, Draft Guidance, September 2006).

The five major human hepatic Cytochrome P450 isoforms, 1A2, 2C9, 2C19, 2D6 and 3A4 were heterologously expressed in E. coli membranes. Each of the five CYPs were incubated with a cocktail of specific substrates; phenacetin, diclofenac, 5-mephenyloin, bufuralol and midazolam, which are predominantly metabolised by CYP 1A2, 2C9, 2C19, 2D6 and 3A4 respectively plus the test compound.

The substrates were incubated, at concentrations equivalent to their respective Km values, and LC-MS-MS (MRM mode) was used in order to follow the formation of their specific metabolites. The ability of the test compound to inhibit the CYP isoforms was determined by following any decrease in the amount of the specific metabolites formed at six different inhibitor concentrations.

The rates of reaction were calculated by measuring MS/MS area units and data analysis was performed by linearising the data using a pseudo Hill plot. The $IC_{50}$ ie the concentration of the test compound that decreases the amount of metabolite formed by 50% was determined.

The mean $pIC_{50}$ values for compound I and Comparative compound I are shown in the table below.

| P450 Isoform | Mean $pIC_{50}$ | |
|---|---|---|
| | Example 1 | Comparative Example 1 |
| CYP1A2 | <5.52 (n = 2) | <4.52 (n = 3) |
| CYP3A4 | 6.33 (n = 2) | 7.88 (n = 3) |
| CYP2C9 | <5.52 (n = 2) | <4.53 (n = 3) |
| CYP2C19 | <5.52 (n = 2) | <4.52 (n = 3) |
| CYP2D6 | <5.52 (n = 2) | 4.87 (n = 3) |

Human Plasma Stability

To determine the half life of the test compound in human plasma, incubations were performed at 37° C. in a shaking water bath. Compound (5 μl of 100 μM stock in MeCN) was spiked into 0.495 mL plasma to give final incubation concentration of 1 μM. Aliquots (50 μl) were withdrawn at various time points (typically 0, 20 & 40 sec, 1, 2, 3, 5 & 10 mins) and quenched into MeCN (3004) followed by analysis for parent compound by LC-MS-MS (MRM mode). The half life was calculated from the decline of test compound peak area over time.

Example 1 (Compound (I)) gave a half life of 0.6 minutes (n=1).

Comparative Example 1 gave a half life of 0.2 minutes (n=1).

The invention claimed is:

1. A compound

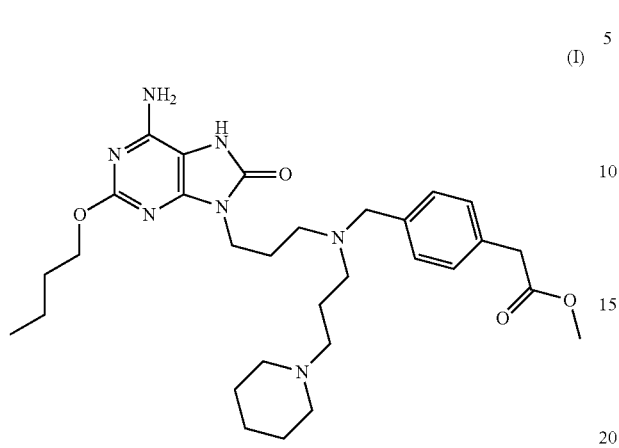

(I)

or a pharmaceutically acceptable salt thereof.

2. The compound of claim 1 in free base form.

3. The pharmaceutically acceptable salt of the compound of claim 2.

4. A pharmaceutical composition comprising the compound, or pharmaceutically acceptable salt thereof, as claimed in any one of claims 1 to 3 in association with a pharmaceutically acceptable adjuvant, diluent or carrier.

5. The pharmaceutical composition according to claim 4, wherein the composition is a topical composition.

6. A process for the preparation of a compound of formula (I), or a pharmaceutically acceptable salt thereof, as defined in claim 1 comprising:

(a)
reacting a compound of the formula (II), or a salt thereof:

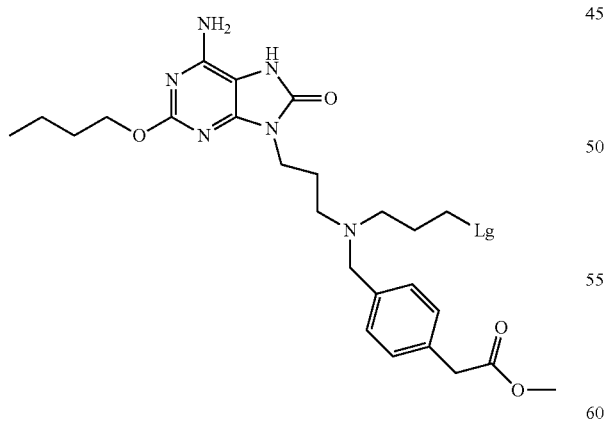

(II)

wherein Lg is a leaving group;
with piperidine; or (b)
reacting a compound of the formula (III), or a salt thereof:

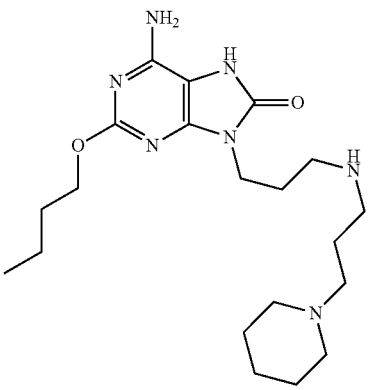

(III)

with methyl (4-formylphenyl)acetate in the presence of a reducing agent;

and thereafter optionally forming a pharmaceutically acceptable salt of a compound of formula (I).

7. A compound of the formula (II), or a salt thereof:

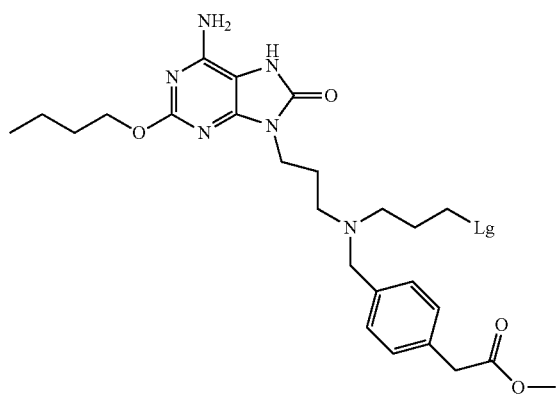

(II)

wherein Lg is a leaving group.

8. A compound of the formula (III):

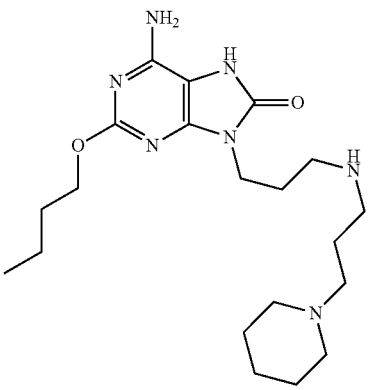

(III)

or a salt thereof.

9. A compound of the formula (IV), or a salt thereof:
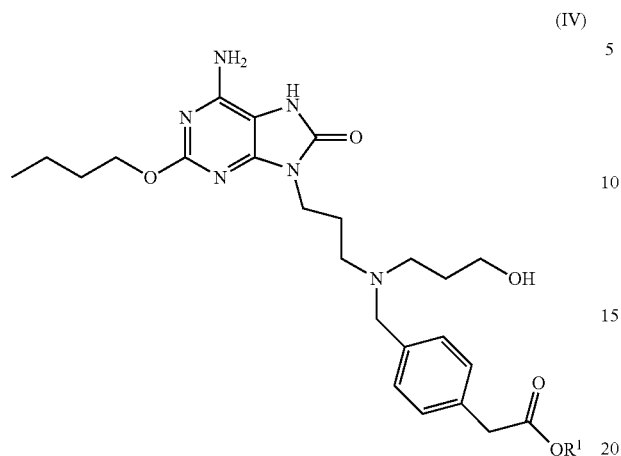
wherein R¹ is hydrogen or methyl.
\* \* \* \* \*

UNITED STATES PATENT AND TRADEMARK OFFICE
CERTIFICATE OF CORRECTION

PATENT NO. : 8,895,570 B2  
APPLICATION NO. : 13/994321  
DATED : November 25, 2014  
INVENTOR(S) : Abbott et al.

Page 1 of 1

It is certified that error appears in the above-identified patent and that said Letters Patent is hereby corrected as shown below:

ON THE TITLE PAGE

(73) Assignee should read:  AstraZeneca AB, Soderitalje (SE)  
                                    Dainippon Sumitomo Pharma Co., Ltd. (JP)

Signed and Sealed this  
First Day of December, 2015

Michelle K. Lee  
*Director of the United States Patent and Trademark Office*